(12) United States Patent
Kelley et al.

(10) Patent No.: US 12,364,599 B2
(45) Date of Patent: Jul. 22, 2025

(54) PROSTHETIC VALVE DEVICE RESISTANT TO BACKFOLDING AND BUCKLING

(71) Applicant: MEDTRONIC, INC., Minneapolis, MN (US)

(72) Inventors: Timothy Kelley, Santa Rosa, CA (US); Victoria Tien, Tustin, CA (US); Alaena Maiorano, Huntington Beach, CA (US); Geoffrey Orth, Sebastopol, CA (US); Mostafa Toloui, Minneapolis, MN (US); Michael Schendel, Andover, MN (US); Anne Breithaupt, Irvine, CA (US); Vickie Pham, Westminster, CA (US); Cathleen Bergin, Hugo, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

(21) Appl. No.: 18/593,136

(22) Filed: Mar. 1, 2024

(65) Prior Publication Data
US 2024/0197470 A1    Jun. 20, 2024

Related U.S. Application Data

(63) Continuation of application No. 17/590,114, filed on Feb. 1, 2022, now Pat. No. 11,951,004.
(Continued)

(51) Int. Cl.
*A61F 2/24* (2006.01)
*A61F 2/07* (2013.01)

(52) U.S. Cl.
CPC .............. *A61F 2/2418* (2013.01); *A61F 2/07* (2013.01); *A61F 2002/075* (2013.01); *A61F 2/2475* (2013.01); *A61F 2/2476* (2020.05); *A61F 2210/0014* (2013.01); *A61F 2220/0075* (2013.01); *A61F 2230/0078* (2013.01);
(Continued)

(58) Field of Classification Search
None
See application file for complete search history.

(56) References Cited

U.S. PATENT DOCUMENTS

| 5,480,424 A | 1/1996 | Cox |
| 5,824,037 A | 10/1998 | Fogarty |

(Continued)

FOREIGN PATENT DOCUMENTS

| GB | 2491477 A | 12/2012 |
| WO | 2012096716 A2 | 7/2012 |
| WO | 2018046917 A1 | 3/2018 |

OTHER PUBLICATIONS

European Search Report issued Nov. 7, 2022 in European Appl. No. 22 158 262.0.

*Primary Examiner* — Rebecca S Preston
(74) *Attorney, Agent, or Firm* — MEDLER, FERRO, WOODHOUSE & MILLS PLLC

(57) ABSTRACT

A prosthesis includes a tubular graft, a prosthetic valve component, an inflow stent, an outflow stent, and a plurality of body stents disposed between the inflow and outflow stents. Each stent is a sinusoidal patterned radially-expandable ring having a first set of crowns and a second set of crowns, with the first set of crowns disposed closer to an inflow end of the tubular graft than the second set of crowns. The prosthesis is configured to be resistant to backfolding and/or buckling during deployment thereof.

20 Claims, 11 Drawing Sheets

Related U.S. Application Data

(60) Provisional application No. 63/232,745, filed on Aug. 13, 2021, provisional application No. 63/154,756, filed on Feb. 28, 2021.

(52) U.S. Cl.
CPC . *A61F 2250/001* (2013.01); *A61F 2250/0018* (2013.01); *A61F 2250/0039* (2013.01); *A61F 2250/0069* (2013.01); *A61F 2250/0098* (2013.01)

(56) References Cited

U.S. PATENT DOCUMENTS

| | | | |
|---|---|---|---|
| 6,027,526 A | 2/2000 | Limon | |
| 6,719,789 B2 | 4/2004 | Cox | |
| 8,801,776 B2 | 8/2014 | House et al. | |
| 9,364,324 B2 | 6/2016 | Rafiee et al. | |
| 10,092,429 B2 | 10/2018 | Krolik | |
| 2003/0023303 A1* | 1/2003 | Palmaz | A61F 2/2418 623/2.18 |
| 2003/0199963 A1 | 10/2003 | Tower et al. | |
| 2003/0199971 A1 | 10/2003 | Tower et al. | |
| 2005/0049667 A1 | 3/2005 | Arbefeuille et al. | |
| 2007/0162103 A1 | 7/2007 | Case et al. | |
| 2010/0049306 A1* | 2/2010 | House | A61F 2/2418 623/1.26 |
| 2014/0200660 A1 | 7/2014 | Savage et al. | |
| 2015/0173898 A1 | 6/2015 | Drasler et al. | |
| 2019/0046316 A1 | 2/2019 | Chen et al. | |
| 2020/0229918 A1 | 7/2020 | Pham et al. | |
| 2021/0085495 A1 | 3/2021 | Bergin et al. | |
| 2021/0346158 A1 | 11/2021 | Orth et al. | |
| 2023/0277305 A1* | 9/2023 | Zamani | A61F 2/2409 623/2.17 |

* cited by examiner

PROSTHETIC VALVE DEVICE RESISTANT TO BACKFOLDING AND BUCKLING

CROSS REFERENCE OF RELATED APPLICATIONS

This application is a continuation of U.S. application Ser. No. 17/590,114, filed on Feb. 1, 2022, now allowed, which claims the benefit of U.S. Provisional Patent Application Ser. No. 63/154,756, filed Feb. 28, 2021, and U.S. Provisional Patent Application Ser. No. 63/232,745, filed Aug. 13, 2021, each of which is hereby incorporated by reference in its entirety for all purposes.

FIELD OF THE INVENTION

The present disclosure relates generally to the treatment of cardiac valve disease using prosthetic valves, and more particularly to a prosthetic valve device configured to be resistant to backfolding and/or buckling during deployment thereof.

BACKGROUND

Natural heart valves, such as aortic valves, mitral valves, pulmonary valves and tricuspid valves, often become damaged by disease in such a manner that they fail to maintain blood flow in a single direction. A malfunctioning heart valve may be stenotic (i.e., heart valve leaflets fail to fully open) or regurgitant (i.e., heart valve leaflets fail to fully close and/or seal). Maintenance of blood flow in a single direction through the heart valve is important for proper flow, pressure and perfusion of blood through the body. Hence, a heart valve that does not function properly may noticeably impair the function of the heart.

Cardiac valve prostheses are well known in the treatment of heart disease to replace malfunctioning heart valves. Heart valve replacement generally has been accomplished by major open heart surgery. This is a serious operation that requires general anesthesia, full cardiopulmonary bypass with complete cessation of cardiopulmonary activity, an extended hospitalization stay, and several more weeks to months of recuperation time. For some patients, open heart surgery is not an option because of the critical condition of the patient, advanced age, existing comorbidities, or other physical limitations.

In addition to replacing malfunctioning heart valves, there is a congenital heart defect patient population that may have fewer than four valves or valves that were removed or rendered incompetent by surgical procedures. These patients tend to be younger with full lives and future valve procedures ahead of them. The patients may present without a typical existing valve annulus and instead have a less discrete, often dilated area where a healthy valve would have typically formed. These dilated areas may also spiral or curve as the patient's heart, other organs, and skeletal anatomy developed around a heart without one or more valves and accommodated based on revised positions, pressures, and flows. In addition to the more traditional adult population, the congenital population may need for a heart valve to deploy in unusually challenging anatomical condition, also requiring hemodynamic performance while conforming to these varied anatomies without regurgitating, buckling, or kinking.

Recently, there has been increasing interest in minimally invasive and percutaneous replacement of cardiac valves, typically by way of catheterization. In minimally invasive procedures, a catheter is used to insert a collapsible bioprosthetic valve into a lumen of a blood vessel via percutaneous entry through a distal blood vessel. In the specific context of pulmonary valve replacement, U.S. Patent Application Publication Nos. 2003/0199971 A1 and 2003/0199963 A1, both filed by Tower et al. and incorporated herein by reference, describe replacing a pulmonary valve with a venous valvular replacement. The replacement pulmonary valve is mounted on a balloon catheter and delivered percutaneously via the vascular system to the location of the failed pulmonary valve and expanded by the balloon against the right ventricular outflow tract, anchoring and sealing the replacement valve.

Pulmonary valve replacement using venous valves is not available to all who might benefit from it due to the relatively narrow size range of available valved segments of veins, for example, with typical sizes available only up to a diameter of about 22 mm. The same limited availability of sizes also applied to pericardial valves. Unfortunately, many patients requiring pulmonary valve replacement are adults and children who have right ventricular outflow tracts that are larger than 22 mm in diameter. This could have resulted, for example, from having previously undergone transannular patch repair of tetralogy of Fallot during infancy. There are other causes, however, for an enlarged right ventricular outflow tract. Thus, venous valvular replacements with a limit of 22 mm diameters, cannot typically be securely implanted within these patients. The same generally applies for pericardial heart valve replacements.

Thus, there is a continuing need to improve upon the devices available for heart valve replacement.

SUMMARY

According to a first embodiment hereof, the present disclosure provides a prosthesis for implantation within a body lumen, the prosthesis having a radially expanded configuration and a radially compressed configuration. The prosthesis includes a tubular graft defining a lumen that extends from an inflow end to an outflow end thereof, a prosthetic valve component disposed within the lumen of the tubular graft, an inflow stent attached to the inflow end of the tubular graft, an outflow stent attached to the outflow end of the tubular graft, and a plurality of body stents attached to the tubular graft and disposed between the inflow stent and the outflow stent. A longitudinal axis of the prosthesis is defined by the lumen of the tubular graft. A first body stent of the plurality of body stents is disposed directly adjacent to the inflow stent and a second body stent of the plurality of body stents is disposed directly adjacent to the outflow stent. Each of the inflow stent, the outflow stent, and each stent of the plurality of body stents is a sinusoidal patterned radially-expandable ring having a first set of crowns and a second set of crowns, with the first set of crowns being disposed closer to the inflow end of the tubular graft than the second set of crowns. The second set of crowns of each of the inflow stent and each body stent of the plurality of body stents is disposed against and attached to the first set of crowns of an adjacent stent. Each of the second body stent and the outflow stent is oriented to extend radially outwards in a direction from the first set of crowns thereof to the second set of crowns thereof. The second body stent is oriented at a first acute angle relative to the longitudinal axis of the prosthesis and the outflow stent is oriented at a second acute angle relative to the longitudinal axis of the prosthesis, the second acute angle being less than the first acute angle.

In an aspect of the first embodiment, and in combination with any other aspects herein, the disclosure provides that the outflow stent is oriented at an angle between 40° and 60° relative to the second body stent.

In an aspect of the first embodiment, and in combination with any other aspects herein, the disclosure provides that the first body stent is oriented to extend radially outwards in a direction from the second set of crowns thereof to the first set of crowns thereof and the first body stent is oriented at an angle between 120° and 140° relative to the longitudinal axis of the prosthesis.

In an aspect of the first embodiment, and in combination with any other aspects herein, the disclosure provides that the plurality of body stents include a third body stent and a fourth body stent disposed between the first and second body stents, the third and fourth body stents being oriented to extend substantially parallel to the longitudinal axis of the prosthesis.

In an aspect of the first embodiment, and in combination with any other aspects herein, the disclosure provides that each of the first body stent, the second body stent, and the outflow stent is formed by a wire having a first diameter that is greater than a second diameter of the remaining stents of the prosthesis. In an embodiment, the first diameter is between 5% and 10% greater than the second diameter.

In an aspect of the first embodiment, and in combination with any other aspects herein, the disclosure provides that the plurality of body stents include a third body stent and a fourth body stent disposed between the first and second body stents. The second set of crowns of the inflow stent is attached to the first set of crowns of the first body stent, the second set of crowns of the first body stent is attached to the first set of crowns of the third body stent, and the second set of crowns of the third body stent is attached to the first set of crowns of the fourth body stent, and the second set of crowns of the fourth body stent is attached to the first set of crowns of the second body stent, and the second set of crowns of the second body stent is attached to the first set of crowns of the outflow stent.

In an aspect of the first embodiment, and in combination with any other aspects herein, the disclosure provides that the second set of crowns of the inflow stent is attached to the first set of crowns of the first body stent by a reinforced connection including at least two axial suture loops extending over adjacent crowns and at least two transverse suture loops extending over the at least two axial suture loops. The second set of crowns of the first body stent is attached to the first set of crowns of the third body stent by a reinforced connection including at least two axial suture loops extending over adjacent crowns and at least two transverse suture loops extending over the at least two axial suture loops. The second set of crowns of the third body stent is attached to the first set of crowns of the fourth body stent by a reinforced connection including at least two axial suture loops extending over adjacent crowns and at least two transverse suture loops extending over the at least two axial suture loops. The second set of crowns of the fourth body stent is attached to the first set of crowns of the second body stent by a reinforced connection including at least two axial suture loops extending over adjacent crowns and at least two transverse suture loops extending over the at least two axial suture loops. The second set of crowns of the second body stent is attached to the first set of crowns of the outflow stent by a reinforced connection including at least two axial suture loops extending over adjacent crowns and at least two transverse suture loops extending over the at least two axial suture loops.

In an aspect of the first embodiment, and in combination with any other aspects herein, the disclosure provides that the second set of crowns of the inflow stent is attached to the first set of crowns of the first body stent by a reinforced connection including exactly three axial suture loops extending over adjacent crowns and exactly two transverse suture loops extending over the three axial suture loops. The second set of crowns of the first body stent is attached to the first set of crowns of the third body stent by a reinforced connection including exactly three axial suture loops extending over adjacent crowns and exactly two transverse suture loops extending over the three axial suture loops. The second set of crowns of the third body stent is attached to the first set of crowns of the fourth body stent by a reinforced connection including exactly three axial suture loops extending over adjacent crowns and exactly two transverse suture loops extending over the three axial suture loops. The second set of crowns of the fourth body stent is attached to the first set of crowns of the second body stent by a reinforced connection including exactly three axial suture loops extending over adjacent crowns and exactly two transverse suture loops extending over the three axial suture loops. The second set of crowns of the second body stent is attached to the first set of crowns of the outflow stent by a reinforced connection including exactly three axial suture loops extending over adjacent crowns and exactly two transverse suture loops extending over the three axial suture loops.

In an aspect of the first embodiment, and in combination with any other aspects herein, the disclosure provides that the tubular graft is formed from a knit fabric.

In an aspect of the first embodiment, and in combination with any other aspects herein, the disclosure provides that the second set of crowns of each of the inflow stent and each body stent of the plurality of body stents is attached to the first set of crowns of an adjacent stent via stitching.

In an aspect of the first embodiment, and in combination with any other aspects herein, the disclosure provides that the second set of crowns of the second body stent is attached to the first set of crowns of the outflow stent with a hinge component. In an embodiment, the hinge component is formed from a radiopaque material.

According to a second embodiment hereof, the present disclosure provides a prosthesis for implantation within a body lumen, the prosthesis having a radially expanded configuration and a radially compressed configuration. The prosthesis includes a tubular graft defining a lumen that extends from an inflow end to an outflow end thereof, a prosthetic valve component disposed within the lumen of the tubular graft, an inflow stent attached to the inflow end of the tubular graft, an outflow stent attached to the outflow end of the tubular graft, and a plurality of body stents attached to the tubular graft and disposed between the inflow stent and the outflow stent. A longitudinal axis of the prosthesis is defined by the lumen of the tubular graft. A first body stent of the plurality of body stents is disposed directly adjacent to the inflow stent and a second body stent of the plurality of body stents is disposed directly adjacent to the outflow stent. Each of the inflow stent, the outflow stent, and each stent of the plurality of body stents is a sinusoidal patterned radially-expandable ring having a first set of crowns and a second set of crowns, with the first set of crowns being disposed closer to the inflow end of the tubular graft than the second set of crowns. The second set of crowns of each of the inflow stent and each body stent of the plurality of body stents is disposed against and attached to the first set of crowns of an adjacent stent. Each of the first body stent, the second body stent, and the outflow stent is formed by a wire having a first diameter that is greater than a second diameter of the remaining stents of the prosthesis. In an embodiment, the first diameter is between 5% and 10% greater than the second diameter.

In an aspect of the second embodiment, and in combination with any other aspects herein, the disclosure provides that the outflow stent is oriented at an angle between 40° and 60° relative to the second body stent.

In an aspect of the second embodiment, and in combination with any other aspects herein, the disclosure provides that the first body stent is oriented to extend radially outwards in a direction from the second set of crowns thereof to the first set of crowns thereof and the first body stent is oriented at an angle between 120° and 140° relative to the longitudinal axis of the prosthesis.

In an aspect of the second embodiment, and in combination with any other aspects herein, the disclosure provides that the plurality of body stents include a third body stent and a fourth body stent disposed between the first and second body stents, the third and fourth body stents being oriented to extend substantially parallel to the longitudinal axis of the prosthesis.

In an aspect of the second embodiment, and in combination with any other aspects herein, the disclosure provides that the plurality of body stents include a third body stent and a fourth body stent disposed between the first and second body stents. The second set of crowns of the inflow stent is attached to the first set of crowns of the first body stent, the second set of crowns of the first body stent is attached to the first set of crowns of the third body stent, and the second set of crowns of the third body stent is attached to the first set of crowns of the fourth body stent, and the second set of crowns of the fourth body stent is attached to the first set of crowns of the second body stent, and the second set of crowns of the second body stent is attached to the first set of crowns of the outflow stent.

In an aspect of the second embodiment, and in combination with any other aspects herein, the disclosure provides that the second set of crowns of the inflow stent is attached to the first set of crowns of the first body stent by a reinforced connection including at least two axial suture loops extending over adjacent crowns and at least two transverse suture loops extending over the at least two axial suture loops. The second set of crowns of the first body stent is attached to the first set of crowns of the third body stent by a reinforced connection including at least two axial suture loops extending over adjacent crowns and at least two transverse suture loops extending over the at least two axial suture loops. The second set of crowns of the third body stent is attached to the first set of crowns of the fourth body stent by a reinforced connection including at least two axial suture loops extending over adjacent crowns and at least two transverse suture loops extending over the at least two axial suture loops. The second set of crowns of the fourth body stent is attached to the first set of crowns of the second body stent by a reinforced connection including at least two axial suture loops extending over adjacent crowns and at least two transverse suture loops extending over the at least two axial suture loops. The second set of crowns of the second body stent is attached to the first set of crowns of the outflow stent by a reinforced connection including at least two axial suture loops extending over adjacent crowns and at least two transverse suture loops extending over the at least two axial suture loops.

In an aspect of the second embodiment, and in combination with any other aspects herein, the disclosure provides that the second set of crowns of the inflow stent is attached to the first set of crowns of the first body stent by a reinforced connection including exactly three axial suture loops extending over adjacent crowns and exactly two transverse suture loops extending over the three axial suture loops. The second set of crowns of the first body stent is attached to the first set of crowns of the third body stent by a reinforced connection including exactly three axial suture loops extending over adjacent crowns and exactly two transverse suture loops extending over the three axial suture loops. The second set of crowns of the third body stent is attached to the first set of crowns of the fourth body stent by a reinforced connection including exactly three axial suture loops extending over adjacent crowns and exactly two transverse suture loops extending over the three axial suture loops. The second set of crowns of the fourth body stent is attached to the first set of crowns of the second body stent by a reinforced connection including exactly three axial suture loops extending over adjacent crowns and exactly two transverse suture loops extending over the three axial suture loops. The second set of crowns of the second body stent is attached to the first set of crowns of the outflow stent by a reinforced connection including exactly three axial suture loops extending over adjacent crowns and exactly two transverse suture loops extending over the three axial suture loops.

In an aspect of the second embodiment, and in combination with any other aspects herein, the disclosure provides that the tubular graft is formed from a knit fabric.

In an aspect of the second embodiment, and in combination with any other aspects herein, the disclosure provides that the second set of crowns of each of the inflow stent and each body stent of the plurality of body stents is attached to the first set of crowns of an adjacent stent via stitching.

In an aspect of the second embodiment, and in combination with any other aspects herein, the disclosure provides that the second set of crowns of the second body stent is attached to the first set of crowns of the outflow stent with a hinge component. In an embodiment, the hinge component is formed from a radiopaque material.

According to a third embodiment hereof, the present disclosure provides a prosthesis for implantation within a body lumen, the prosthesis having a radially expanded configuration and a radially compressed configuration. The prosthesis includes a tubular graft defining a lumen that extends from an inflow end to an outflow end thereof, a prosthetic valve component disposed within the lumen of the tubular graft, an inflow stent attached to the inflow end of the tubular graft, an outflow stent attached to the outflow end of the tubular graft, and a plurality of body stents attached to the tubular graft and disposed between the inflow stent and the outflow stent. A longitudinal axis of the prosthesis is defined by the lumen of the tubular graft. A first body stent of the plurality of body stents is disposed directly adjacent to the inflow stent and a second body stent of the plurality of body stents is disposed directly adjacent to the outflow stent. Each of the inflow stent, the outflow stent, and each stent of the plurality of body stents is a sinusoidal patterned radially-expandable ring having a first set of crowns and a second set of crowns, with the first set of crowns being disposed closer to the inflow end of the tubular graft than the second set of crowns. The second set of crowns of each of the inflow stent and each body stent of the plurality of body stents is disposed against and attached to the first set of crowns of an adjacent stent by a reinforced connection including at least two axial suture loops extending over adjacent crowns and at least two transverse suture loops extending over the at least two axial suture loops.

In an aspect of the third embodiment, and in combination with any other aspects herein, the disclosure provides that the outflow stent is oriented at an angle between 40° and 60° relative to the second body stent.

In an aspect of the third embodiment, and in combination with any other aspects herein, the disclosure provides that the first body stent is oriented to extend radially outwards in a direction from the second set of crowns thereof to the first set of crowns thereof and the first body stent is oriented at an angle between 120° and 140° relative to the longitudinal axis of the prosthesis.

In an aspect of the third embodiment, and in combination with any other aspects herein, the disclosure provides that the plurality of body stents include a third body stent and a fourth body stent disposed between the first and second body stents, the third and fourth body stents being oriented to extend substantially parallel to the longitudinal axis of the prosthesis.

In an aspect of the third embodiment, and in combination with any other aspects herein, the disclosure provides that the plurality of body stents include a third body stent and a fourth body stent disposed between the first and second body stents. The second set of crowns of the inflow stent is attached to the first set of crowns of the first body stent, the second set of crowns of the first body stent is attached to the first set of crowns of the third body stent, the second set of crowns of the third body stent is attached to the first set of crowns of the fourth body stent, the second set of crowns of the fourth body stent is attached to the first set of crowns of the second body stent, and the second set of crowns of the second body stent is attached to the first set of crowns of the outflow stent.

In an aspect of the third embodiment, and in combination with any other aspects herein, the disclosure provides that the second set of crowns of the inflow stent is attached to the first set of crowns of the first body stent by exactly three axial suture loops extending over adjacent crowns and exactly two transverse suture loops extending over the three axial suture loops, the second set of crowns of the first body stent is attached to the first set of crowns of the third body stent by exactly three axial suture loops extending over adjacent crowns and exactly two transverse suture loops extending over the three axial suture loops, the second set of crowns of the third body stent is attached to the first set of crowns of the fourth body stent by exactly three axial suture loops extending over adjacent crowns and exactly two transverse suture loops extending over the three axial suture loops, the second set of crowns of the fourth body stent is attached to the first set of crowns of the second body stent by exactly three axial suture loops extending over adjacent crowns and exactly two transverse suture loops extending over the three axial suture loops, and the second set of crowns of the second body stent is attached to the first set of crowns of the outflow stent by exactly three axial suture loops extending over adjacent crowns and exactly two transverse suture loops extending over the three axial suture loops.

In an aspect of the third embodiment, and in combination with any other aspects herein, the disclosure provides that the tubular graft is formed from a knit fabric.

In an aspect of the third embodiment, and in combination with any other aspects herein, the disclosure provides that each of the first body stent, the second body stent, and the outflow stent is formed by a wire having a first diameter that is greater than a second diameter of the remaining stents of the prosthesis, the first diameter being between 5% and 10% greater than the second diameter.

In an aspect of the third embodiment, and in combination with any other aspects herein, the disclosure provides that each of the second body stent and the outflow stent is oriented to extend radially outwards in a direction from the first set of crowns thereof to the second set of crowns thereof. The second body stent is oriented at a first acute angle relative to the longitudinal axis of the prosthesis and the outflow stent is oriented at a second acute angle relative to the longitudinal axis of the prosthesis, the second acute angle being less than the first acute angle.

In an aspect of the third embodiment, and in combination with any other aspects herein, the disclosure provides that the second body stent is oriented to extend radially outwards in a direction from the first set of crowns thereof to the second set of crowns thereof, the second body stent being oriented at a first acute angle relative to the longitudinal axis of the prosthesis. The outflow stent is oriented substantially parallel relative to the longitudinal axis of the prosthesis.

According to a fourth embodiment hereof, the present disclosure provides a prosthesis for implantation within a body lumen, the prosthesis having a radially expanded configuration and a radially compressed configuration. The prosthesis includes a tubular graft defining a lumen that extends from an inflow end to an outflow end thereof, a prosthetic valve component disposed within the lumen of the tubular graft, an inflow stent attached to the inflow end of the tubular graft, an outflow stent attached to the outflow end of the tubular graft, and a plurality of body stents attached to the tubular graft and disposed between the inflow stent and the outflow stent. A longitudinal axis of the prosthesis is defined by the lumen of the tubular graft. A first body stent of the plurality of body stents is disposed directly adjacent to the inflow stent and a second body stent of the plurality of body stents is disposed directly adjacent to the outflow stent. Each of the inflow stent, the outflow stent, and each stent of the plurality of body stents is a sinusoidal patterned radially-expandable ring having a first set of crowns and a second set of crowns, with the first set of crowns being disposed closer to the inflow end of the tubular graft than the second set of crowns. The second set of crowns of each of the inflow stent and each body stent of the plurality of body stents is disposed against and attached to the first set of crowns of an adjacent stent. The second body stent is oriented to extend radially outwards in a direction from the first set of crowns thereof to the second set of crowns thereof, the second body stent being oriented at a first acute angle relative to the longitudinal axis of the prosthesis. The outflow stent is oriented substantially parallel relative to the longitudinal axis of the prosthesis.

In an aspect of the fourth embodiment, and in combination with any other aspects herein, the disclosure provides that the outflow stent is oriented at an angle between 40° and 60° relative to the second body stent.

In an aspect of the fourth embodiment, and in combination with any other aspects herein, the disclosure provides that the first body stent is oriented to extend radially outwards in a direction from the second set of crowns thereof to the first set of crowns thereof and the first body stent is oriented at an angle between 120° and 140° relative to the longitudinal axis of the prosthesis.

In an aspect of the fourth embodiment, and in combination with any other aspects herein, the disclosure provides that the plurality of body stents include a third body stent and a fourth body stent disposed between the first and second body stents, the third and fourth body stents being oriented to extend substantially parallel to the longitudinal axis of the prosthesis.

In an aspect of the fourth embodiment, and in combination with any other aspects herein, the disclosure provides that each of the first body stent, the second body stent, and the outflow stent is formed by a wire having a first diameter that is greater than a second diameter of the remaining stents of the prosthesis. In an embodiment, the first diameter is between 5% and 10% greater than the second diameter.

In an aspect of the fourth embodiment, and in combination with any other aspects herein, the disclosure provides that the plurality of body stents include a third body stent and a fourth body stent disposed between the first and second body stents. The second set of crowns of the inflow stent is attached to the first set of crowns of the first body stent, the second set of crowns of the first body stent is attached to the first set of crowns of the third body stent, and the second set of crowns of the third body stent is attached to the first set of crowns of the fourth body stent, and the second set of crowns of the fourth body stent is attached to the first set of crowns of the second body stent, and the second set of crowns of the second body stent is attached to the first set of crowns of the outflow stent.

In an aspect of the fourth embodiment, and in combination with any other aspects herein, the disclosure provides that the second set of crowns of the inflow stent is attached to the first set of crowns of the first body stent by a reinforced connection including at least two axial suture loops extending over adjacent crowns and at least two transverse suture loops extending over the at least two axial suture loops. The second set of crowns of the first body stent is attached to the first set of crowns of the third body stent by a reinforced connection including at least two axial suture loops extending over adjacent crowns and at least two transverse suture loops extending over the at least two axial suture loops. The second set of crowns of the third body stent is attached to the first set of crowns of the fourth body stent by a reinforced connection including at least two axial suture loops extending over adjacent crowns and at least two transverse suture loops extending over the at least two axial suture loops. The second set of crowns of the fourth body stent is attached to the first set of crowns of the second body stent by a reinforced connection including at least two axial suture loops extending over adjacent crowns and at least two transverse suture loops extending over the at least two axial suture loops. The second set of crowns of the second body stent is attached to the first set of crowns of the outflow stent by a reinforced connection including at least two axial suture loops extending over adjacent crowns and at least two transverse suture loops extending over the at least two axial suture loops.

In an aspect of the fourth embodiment, and in combination with any other aspects herein, the disclosure provides that the second set of crowns of the inflow stent is attached to the first set of crowns of the first body stent by a reinforced connection including exactly three axial suture loops extending over adjacent crowns and exactly two transverse suture loops extending over the three axial suture loops. The second set of crowns of the first body stent is attached to the first set of crowns of the third body stent by a reinforced connection including exactly three axial suture loops extending over adjacent crowns and exactly two transverse suture loops extending over the three axial suture loops. The second set of crowns of the third body stent is attached to the first set of crowns of the fourth body stent by a reinforced connection including exactly three axial suture loops extending over adjacent crowns and exactly two transverse suture loops extending over the three axial suture loops. The second set of crowns of the fourth body stent is attached to the first set of crowns of the second body stent by a reinforced connection including exactly three axial suture loops extending over adjacent crowns and exactly two transverse suture loops extending over the three axial suture loops. The second set of crowns of the second body stent is attached to the first set of crowns of the outflow stent by a reinforced connection including exactly three axial suture loops extending over adjacent crowns and exactly two transverse suture loops extending over the three axial suture loops.

In an aspect of the fourth embodiment, and in combination with any other aspects herein, the disclosure provides that the tubular graft is formed from a knit fabric.

In an aspect of the fourth embodiment, and in combination with any other aspects herein, the disclosure provides that the second set of crowns of each of the inflow stent and each body stent of the plurality of body stents is attached to the first set of crowns of an adjacent stent via stitching.

In an aspect of the fourth embodiment, and in combination with any other aspects herein, the disclosure provides that the second set of crowns of the second body stent is attached to the first set of crowns of the outflow stent with a hinge component. In an embodiment, the hinge component is formed from a radiopaque material.

BRIEF DESCRIPTION OF THE DRAWINGS

The accompanying figures, which are incorporated herein, form part of the specification and illustrate embodiments of a delivery system. Together with the description, the figures further explain the principles of and enable a person skilled in the relevant arts to make, use, and implant the prosthesis described herein. In the drawings, like reference numbers indicate identical or functionally similar elements.

DETAILED DESCRIPTION OF THE INVENTION

Figure 1:
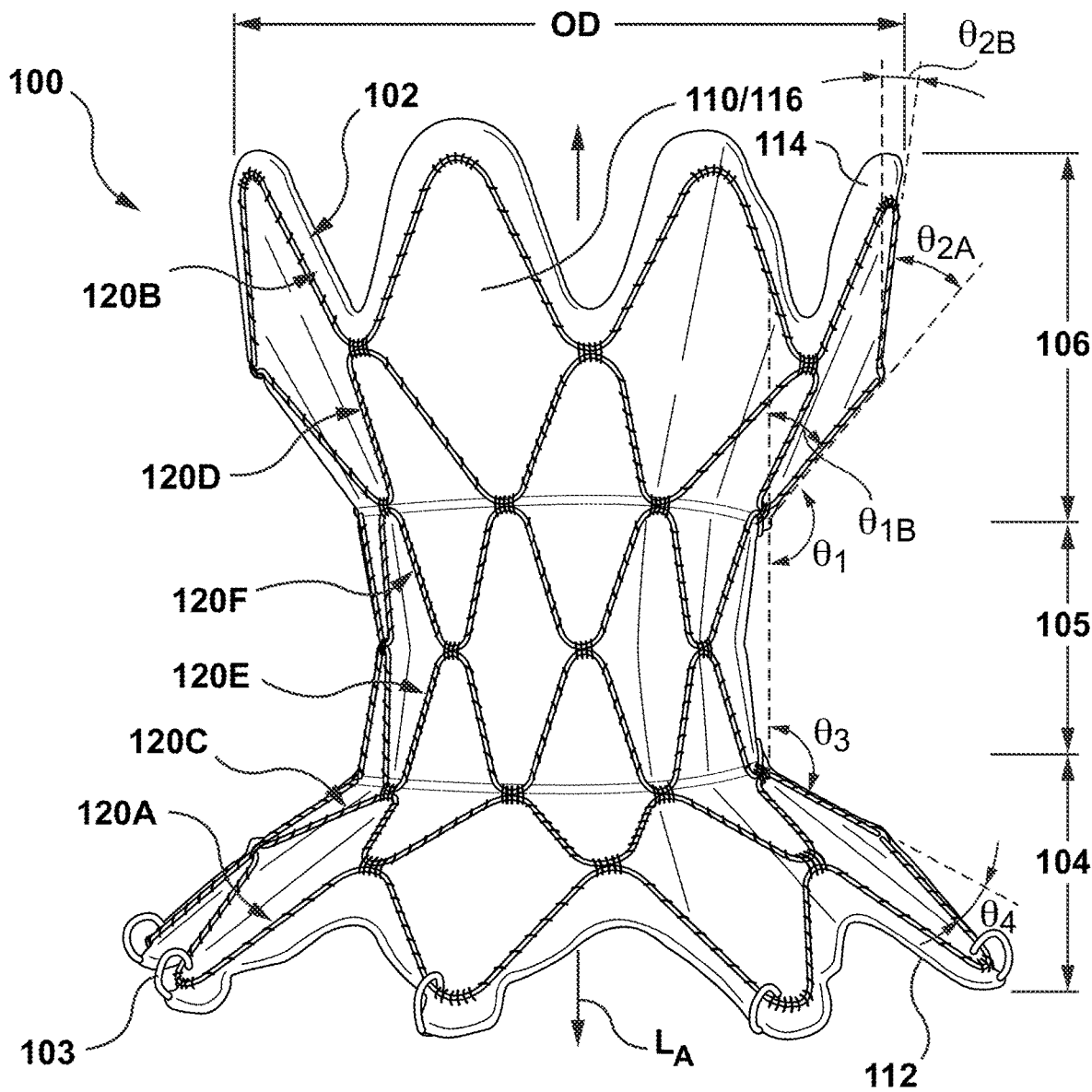
FIG. 1 is a side view of a prosthetic valve device according to an aspect of the present disclosure, wherein the prosthetic valve device is shown in its radially expanded or deployed configuration.

Specific embodiments of the present invention are now described with reference to the figures, wherein like reference numbers indicate identical or functionally similar elements. Unless otherwise indicated, the terms "distal" and "proximal", when used in the following description to refer to a shaft, a sheath, or a delivery device, are with respect to a position or direction relative to the treating clinician. Thus, "distal" and "distally" refer to positions distant from, or in a direction away from the treating clinician, and the terms "proximal" and "proximally" refer to positions near, or in a direction toward the treating clinician. The terms "distal" and "proximal", when used in the following description to refer to a device to be implanted into a vessel, such as a heart prosthetic valve device, are used with reference to the direction of blood flow. Thus, "distal" and "distally" refer to positions in a downstream direction with respect to the direction of blood flow, and the terms "proximal" and "proximally" refer to positions in an upstream direction with respect to the direction of blood flow.

In addition, the term "self-expanding" is used in the following description with reference to one or more stent structures of the prostheses hereof and is intended to convey that the structures are shaped or formed from a material that can be provided with a mechanical memory to return the structure from a radially compressed or constricted radially compressed configuration to a radially expanded deployed configuration. Non-exhaustive illustrative self-expanding materials include stainless steel, a pseudo-clastic metal such as a nickel titanium alloy or nitinol, various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

This disclosure relates to a prosthetic valve device that is configured to reduce backfolding and/or buckling when deployed. If backfolding and/or buckling occur when the prosthetic valve device is deployed, the prosthetic valve device is not deployed to its intended deployed or expanded configuration which impacts the performance of the prosthetic valve device. Particularly, backfolding and/or buckling of the prosthetic valve device may result in undesirable paravalvular leakage, device migration and/or device embolization. Certain deployment techniques may sometimes be utilized to reduce backfolding and/or buckling of a prosthetic valve device during deployment, but such deployment techniques are user dependent and cannot be utilized with all patients, thereby dropping the total patient coverage for the prosthetic valve device. Thus, it is preferable to utilize a prosthetic valve device that is configured to reduce backfolding and/or buckling without the need for any specialized deployments techniques.

Figure 2:
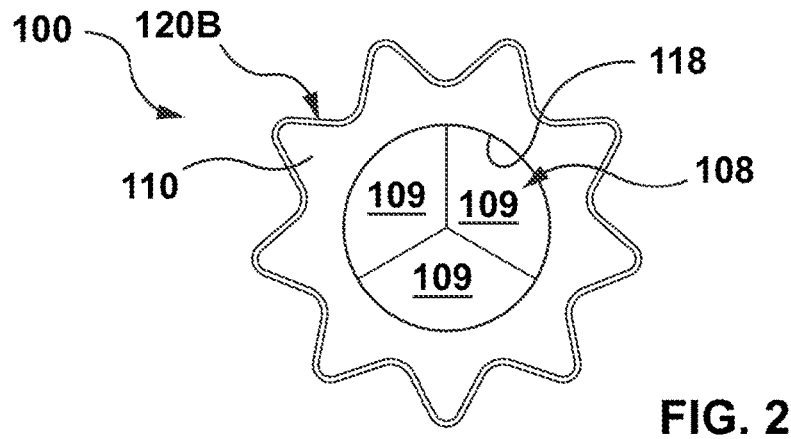
FIG. 2 is an end view of the prosthetic valve device of FIG. 1.

A side view and an end view of a prosthetic valve device 100 in accordance with an aspect of the disclosure are shown in FIG. 1 and FIG. 2, respectively. The prosthetic valve device 100 is configured to be radially compressed into a reduced-diameter crimped configuration (not shown) for delivery within a vasculature and to return to a radially expanded or deployed configuration, which is shown in FIG. 1 and FIG. 2. Stated another way, the prosthetic valve device 100 has a radially compressed configuration for delivery within a vasculature and a radially expanded configuration for deployment at a treatment site. In an embodiment, the treatment site is a native heart valve. However, other treatment sites are contemplated herein, including but not limited to a treatment site within the inferior vena cava (IVC) or the superior vena cava (SVC) for tricuspid insufficiency as well as a treatment site in which a native heart valve was previously removed, rendered incompetent by surgical procedures, or did not properly form. In accordance with embodiments hereof, when in the crimped configuration, the prosthetic valve device 100 has a low profile suitable for delivery to and deployment within a native heart valve via a suitable delivery catheter that may be tracked to the treatment site via any suitable approach. In an embodiment in which the prosthetic valve device 100 is delivered to the right ventricular outflow tract, the delivery catheter is tracked or delivered to the right ventricular outflow tract in the direction or with the flow of blood. The prosthetic valve device 100 includes an expandable frame 102, a tubular graft 110, and a prosthetic valve component 108 disposed within and secured to the frame 102 and/or the tubular graft 110.

The tubular graft 110 has a first or inflow end 112, a second or outflow end 114, and a body 116 therebetween which defines a central lumen 118 that extends from the inflow end 112 to the outflow end 114. The central lumen 118 may also be considered a central lumen through the prosthetic valve device 100. A longitudinal axis $L_A$ of the prosthetic valve device 100 is defined by or extends parallel to the central lumen 118 of the tubular graft 110. In an embodiment, the inflow end 112 of tubular graft 110 may be referred to as a proximal end of tubular graft 110 and a proximal end of prosthetic valve device 100, which may be the end that is coupled to a delivery system, and the outflow end 114 of tubular graft 110 may be referred to as a distal end of graft 114 and a distal end of prosthetic valve device 100. The tubular graft 110 encloses or lines the frame 102 as would be known to one of ordinary skill in the art of prosthetic tissue valve construction. The tubular graft 110 may be a natural or biological material such as pericardium or another membranous tissue such as intestinal submucosa. Alternatively, the tubular graft 110 may be a knit or low-porosity woven fabric, such as polyester, Dacron fabric, or PTFE, which creates a one-way fluid passage when attached to the stent. In one embodiment, the tubular graft 110 may be a knit or woven polyester, such as a polyester or PTFE knit, which can be utilized when it is desired to provide a medium for tissue ingrowth and the ability for the fabric to stretch to conform to a curved surface, or may instead be ultra-high molecular weight polyethylene (UHMWPE), cotton, or the like. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example.

In embodiments hereof, the frame 102 is self-expanding or self-expandable to return to the radially expanded configuration from the radially compressed configuration. The prosthetic valve device 100 is compressible to be mounted into a delivery system and expandable to fit a desired body lumen, such as the right ventricular outflow tract, for example. In the embodiment depicted in FIG. 1, the frame 102 has an expanded, longitudinally asymmetric hourglass configuration including three longitudinal sections or portions of a relatively enlarged inflow end 104, a relatively enlarged outflow end 106, and a midportion 105 extending between the first and second ends 104, 106. The inflow end 104 may also be referred to herein as the proximal or first end, and the outflow end 106 may also be referred to herein as the distal or second end. The midportion 105 is generally cylindrical in shape with a smaller diameter than the inflow and outflow ends 104, 106. One advantage of the midportion 105 having a smaller diameter than the inflow and outflow ends 104, 106 is to allow at least a portion of the midportion 105 of the frame 102 to hold or retain the prosthetic valve component 108 in the central lumen 118 of the tubular graft 110, when the prosthetic valve component 108 has a smaller diameter than the lumen in which the prosthetic valve device 100 is to be placed. The larger diameters of the inflow and outflow ends 104, 106 allow the prosthetic valve device 100 to be secured in place in a tubular organ, or a valved anatomic site, having a diameter larger than that of the prosthetic valve component 108 but smaller than the expanded diameter of the inflow and outflow ends 104, 106. The inflow and outflow ends 104, 106 are also shown to be flared, such that they gradually increase in diameter from where the inflow and outflow 104, 106 extend from the midportion 105. The angle at which the inflow and outflow ends 104, 106 are flared from the midportion 105 will be described in more detail herein.

The frame 102 includes a plurality of radially-compressible stents or scaffolds, collectively referred to herein as stents 120, that is coupled to the tubular graft 110 for supporting the tubular graft 110 and is operable to self-expand into apposition with an interior wall of a body vessel (not shown). In the embodiment depicted in FIG. 1, the prosthetic valve device 100 is shown in its radially expanded or deployed configuration and includes a series of six independent or separate stents 120. Although shown with six stents 120, it will be understood by one of ordinary skill in the art that the prosthetic valve device 100 may include a greater or smaller number of stents depending upon the desired length of the prosthetic valve device 100 and/or the intended application thereof. The stents 120 are coupled to the tubular graft 110 by stitches or other means known to those of skill in the art. In the embodiment shown in FIG. 1, the stents 120 are coupled to an outside surface of the tubular graft 110. However, the stents 120 may alternatively be coupled to an inside surface of the tubular graft 110. The stents 120 have sufficient radial spring force and flexibility to conformingly engage the prosthetic valve device 100 with the surrounding native anatomy, i.e., to provide a leak-resistant seal.

For description purposes only, the stent that is coupled adjacent and proximate to the inflow end 112 of the tubular graft 110 is referred to herein as an inflow stent 120A and the stent that is coupled adjacent and proximate to the outflow end 114 of the tubular graft 110 is referred to herein as outflow stent 120B. The frame 102 also includes a plurality of body stents 120C, 120D, 120E, 120F that are attached to the tubular graft 110 and disposed between the inflow stent 120A and the outflow stent 120B. A first body stent 120C of the plurality of body stents is disposed directly adjacent to the inflow stent 120A and a second body stent 120D of the plurality of body stents is disposed directly adjacent to the outflow stent 120B. The inflow end 104 of the frame 102 includes the inflow stent 120A and the first body stent 120C, the midportion 105 of the frame 102 includes the third body stent 120E and the fourth body stent 120F, and the outflow end 106 of the frame 102 includes the outflow stent 120B and the second body stent 120D. The third and fourth body stents 120E, 120F are longitudinally disposed between the first and second body stents 120C, 120D, and are oriented to extend substantially parallel to the longitudinal axis $L_A$ of the prosthetic valve device 100. As used herein with respect to the third and fourth body stents 120E, 120F, "substantially parallel" to the longitudinal axis $L_A$ of the prosthetic valve device 100 includes angles up to 10° relative to the longitudinal axis $L_A$ of the prosthetic valve device 100. More particularly, in an embodiment, the third and fourth body stents 120E, 120F may be formed prior to assembly with a vertical orientation that is parallel to the longitudinal axis $L_A$ of the prosthetic valve device 100. However, after assembly (i.e., attachment to the tubular graft 110 and the adjacent body stents), the third and fourth body stents 120E, 120F may extend at a slight angle with respect to the longitudinal axis $L_A$ of the prosthetic valve device 100. In an embodiment, after assembly, the fourth body stent 120F may be angled slightly radially outward in a direction from the first set of crowns 122F thereof to the second set of crowns 126F at an angle between 5° and 10° relative to the longitudinal axis $L_A$ of the prosthetic valve device 100. In an embodiment, after assembly, the third body stent 120E may be angled slightly radially outward in a direction from the second set of crowns 126E thereof to the first set of crowns 122E thereof at an angle between 5° and 10° relative to the longitudinal axis $L_A$ of the prosthetic valve device 100.

Each of the inflow stent 120A, the outflow stent 120B, and each stent of the plurality of body stents 120C, 120D, 120E, 120F is constructed from a self-expanding or spring material, including but not limited to nickel titanium alloys such as Nitinol™. Each of the inflow stent 120A, the outflow stent 120B, and each stent of the plurality of body stents 120C, 120D, 120E, 120F is a sinusoidal patterned radially-expandable ring having a first set of bends or crowns 122A, 122B, 122C, 122D, 122E, 122F (collectively referred to herein as the first set of crowns 122) and a second set of bends crowns 126A, 126B, 126C, 126D, 126E, 126F (collectively referred to herein as the second set of crowns 126), with a strut or straight segment 124A, 124B, 124C, 124D, 124E, 124F (collectively referred to herein as the struts 124) being formed between a pair of opposing crowns. Stated another way, each crown of the first and second sets of crowns 122, 126 is a curved segment or bend extending or formed between a pair of opposing struts 124. Collectively, the first set of crowns 122, the struts 124, and the second set of bends crowns 126 form or define the sinusoidal pattern of each stent. The first set of crowns 122 opposes the second set of crowns 126, with the first set of crowns 122 being disposed closer to the inflow end 112 of the tubular graft 110 than the second set of crowns 126. The second set of crowns 126A, 126C, 126D, 126D, 126E, 126F of each of the inflow stent 120A and each body stent of the plurality of body stents 120C, 120D, 120E, 120F are disposed against and attached to the first set of crowns of an adjacent stent via stitching. Methods of attachment between each pair of adjacent stents are described in more detail with respect to FIGS. 9-16 below. Each of the inflow stent 120A, the outflow stent 120B, and each stent of the plurality of body stents 120C, 120D, 120E, 120F is manufactured or formed in their radially expanded or deployed configurations, and is constructed from a wire that is shaped into the sinusoidal patterned ring described above. The wire for forming stents 120 may have a circular cross-section. In another embodiment hereof (not shown), one or more of the inflow stent 120A, the outflow stent 120B, and each stent of the plurality of body stents 120C, 120D, 120E, 120F may be cut from tubing and shape set into the desired configuration, with adjacent stents being subsequently welded or otherwise attached to each other at abutting crowns. Further, in another embodiment hereof (not shown), the frame 102 may be constructed as a unitary component that is cut from tubing and shape set in the desired configuration.

The first set of crowns 122A of the inflow stent 120A may be considered endmost inflow crowns and are disposed at the inflow end of the frame 102. The number of endmost inflow crowns may vary according to size and application and may range, for example, between 6-15 crowns. In an embodiment, the inflow stent 120A has a total of nine endmost inflow crowns, as best shown in the end view of FIG. 2. However, the configuration of the frame 102 is exemplary and other stent configurations are contemplated. Similarly, the second set of crowns 126B of the outflow stent 120B may be considered endmost outflow crowns and are disposed at the outflow end of the frame 102. The number of endmost outflow crowns may also vary according to size and application and may range, for example, between 6-15 crowns. In an embodiment, the outflow stent 120B has a total of nine endmost outflow crowns.

Any portion of the frame 102 described herein as an element of a heart valve prothesis 100 may be made from any number of suitable biocompatible materials, e.g., stainless steel, nickel titanium alloys such as Nitinol™, cobalt chromium alloys such as MP35N, other alloys such as ELGILOY® (Elgin, Ill.), various polymers, pyrolytic carbon, silicone, polytetrafluorochthylene (PTFE), or any number of other materials or combination of materials. A suitable biocompatible material would be selected to provide the prosthetic heart valve 100 to be configured to be compressed into a reduced-diameter crimped configuration for transcatheter delivery to a treatment site, whereby release from a delivery catheter returns the prosthesis to the radially expanded or deployed configuration.

As previously mentioned, the prosthetic valve device 100 includes the prosthetic valve component 108 positioned or disposed within the center lumen 118 of the tubular graft 110. The prosthetic valve component 108 is attached to (i.e., affixed to, held by, retained by, etc.) the frame 102 along its ends and is sutured or otherwise attached within the frame 102 and/or the tubular graft 110. The prosthetic valve component 108 is capable of blocking flow in one direction to regulate flow there through via valve leaflets 109 that may form a bicuspid or tricuspid replacement valve. In the embodiment of FIGS. 1 and 2, the prosthetic valve component 108 includes three leaflets 109 or a tricuspid leaflet configuration, although a bicuspid leaflet configuration may alternatively be used in embodiments hereof. The leaflets 109 may be formed of a variety of materials including biological materials and polymers. Biological material includes homograft, allograft, or xenograft, with xenograft being common and well accepted and usually from bovine, ovine, swine or porcine pericardium, or a combination thereof. Polymers include expanded TEFLON™ polymers, high density polyethylene, polyurethane, and combinations thereof. Some examples of prosthetic valve components that may be used in the invention are described in U.S. Pat. Nos. 6,719,789 and 5,480,424, issued to Cox, which are incorporated herein by reference. With certain prosthetic leaflet materials, it may be desirable to coat one or both sides of the replacement valve leaflet with a material that will prevent or minimize overgrowth. It is further desirable that the prosthetic leaflet material is durable and not subject to stretching, deforming, or fatigue.

For delivery, the prosthetic valve device 100 is radially compressed into a reduced-diameter crimped configuration onto a delivery system (not shown) for delivery within a vasculature. As known in the art, the delivery system includes an inner shaft that receives the prosthetic valve device 100 on a distal portion thereof and an outer sheath or capsule that is configured to compressively retain the prosthetic valve device 100 on the distal portion of the inner shaft during delivery. Stated another way, the outer sheath or capsule surrounds and constrains the prosthetic valve device 100 in the radially compressed or crimped configuration. An exemplary delivery system for delivering the prosthetic valve device 100 is described in U.S. Pat. No. 9,364,324 to Rafice et al., which is hereby incorporated by reference in its entirety. However, it will be apparent to one of ordinary skill in the art that other delivery systems may be utilized and that the components of the delivery system may vary depending upon the configuration and structure of the prosthetic valve device that is being delivered.

The prosthetic valve device 100 includes a plurality of attachment members 103 on or near the inflow end 104 for coupling the prosthetic valve device 100 to the delivery system. Such attachment members 103 may be loops formed from sutures, may be formed from the material used to form part of the frame 102, or other materials. The attachment members 103 may be made of loops formed from UHMWPE thread, for one example, since this material advantageously has the properties of being durable and lubricous, as well as hydrophobic, which can help to minimize swelling or clotting due to contact with blood. However, other materials may be used that comprise some or all of these attachment properties. Other attachment members besides loops are also contemplated by the invention. Such attachment members are configured to connect, fasten or attach the prosthetic valve device 100 to a delivery system, allow for collapse of the prosthetic valve device 100 for insertion into the body, and also are configured to be selectively disengaged or disconnected from the delivery system in order to release the prosthetic valve device 100 at a desired anatomic site. Further, in another embodiment, the prosthetic valve device 100 may include a second plurality of attachment members on or near the outflow end 106 for controlled release of the outflow end as further described in U.S. Prov. Appl. No. 63/022,016, filed on May 8, 2020, herein incorporated by reference in its entirety.

Figure 3:
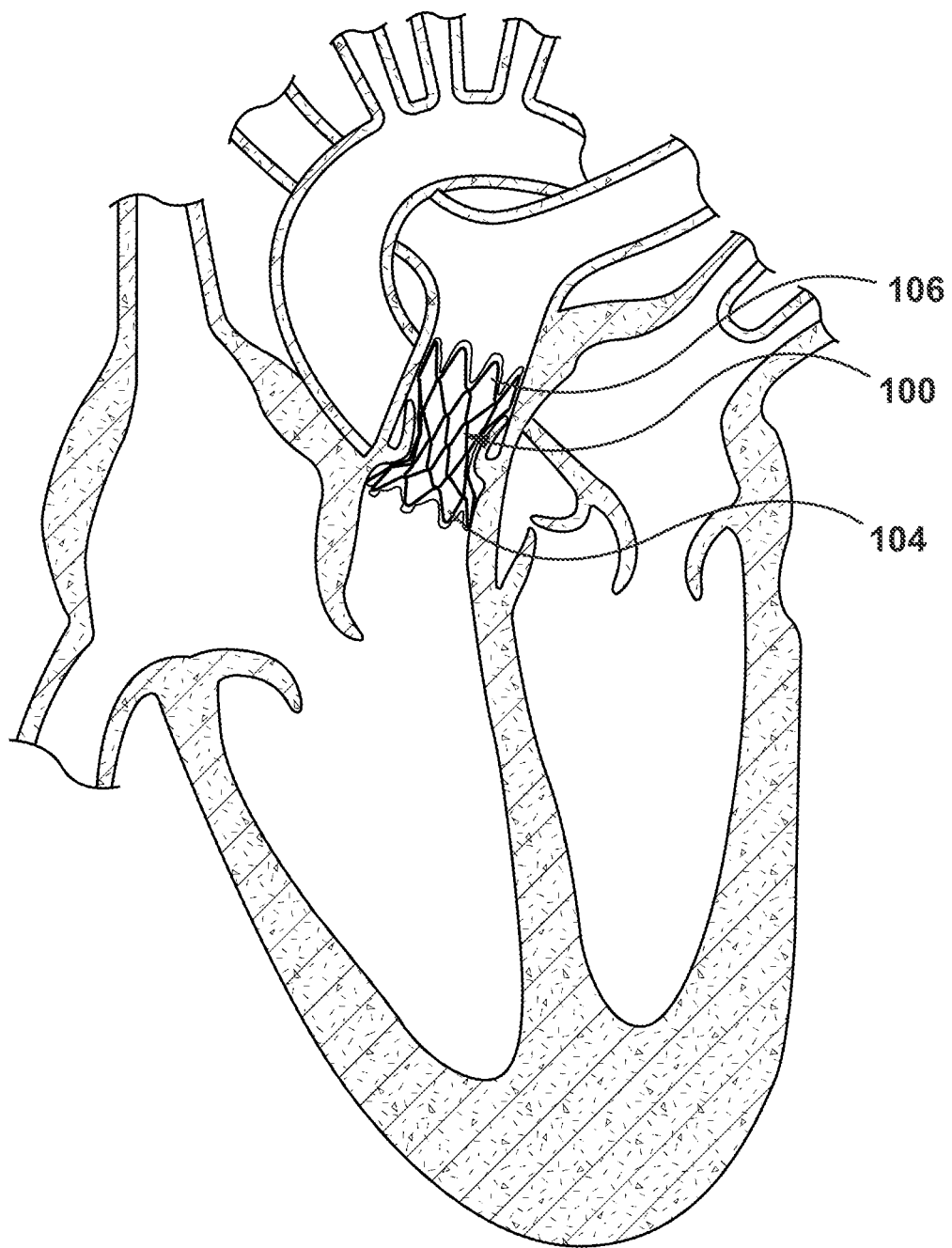
FIG. 3 depicts the prosthetic valve device of FIG. 1 implanted in situ at a treatment site according to an aspect of the present disclosure, wherein the treatment site is a native right ventricular outflow tract (RVOT).
Figure 4A:
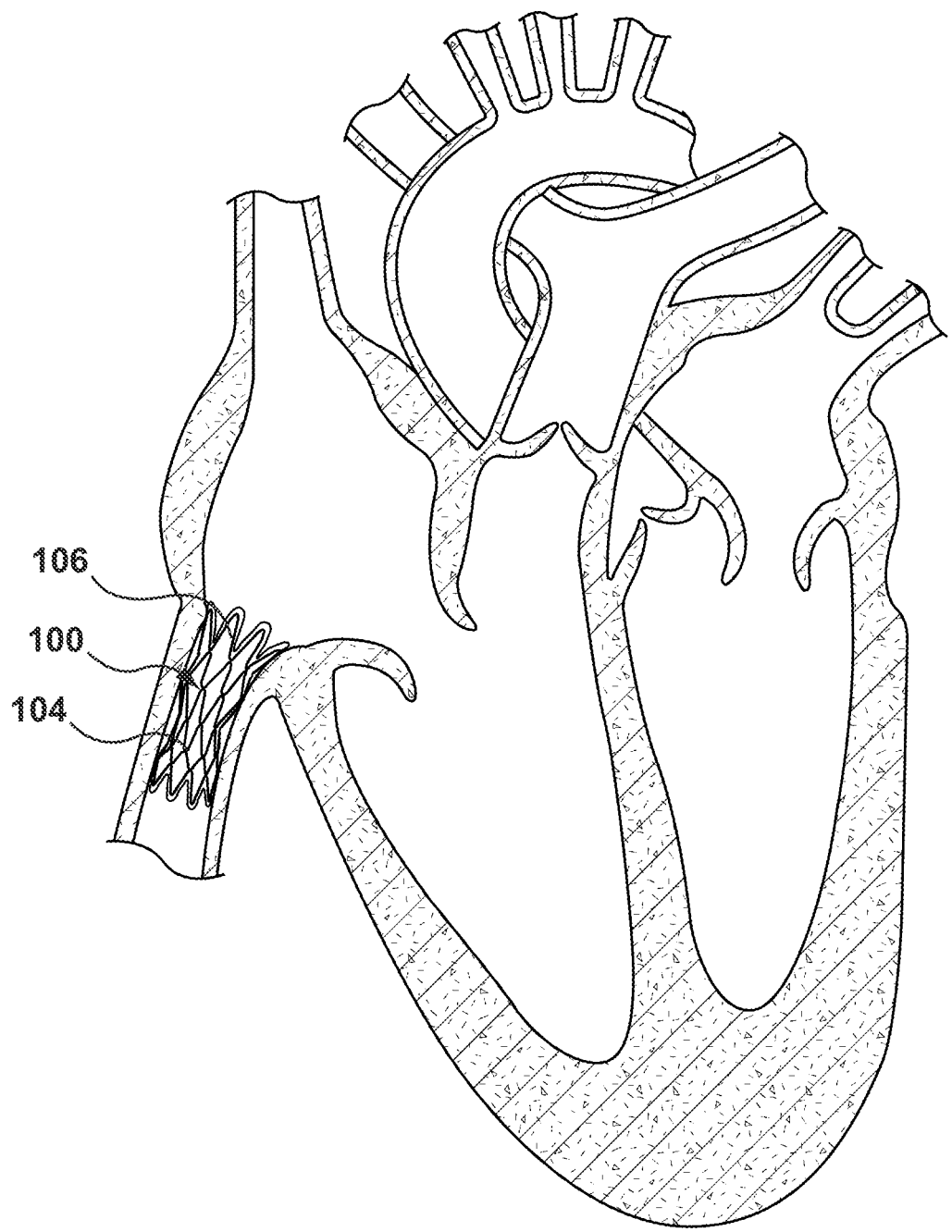
FIG. 4A depicts the prosthetic valve device of FIG. 1 implanted in situ at a treatment site according to another aspect of the present disclosure, wherein the treatment site is an Inferior Vena Cava (IVC).
Figure 4B:
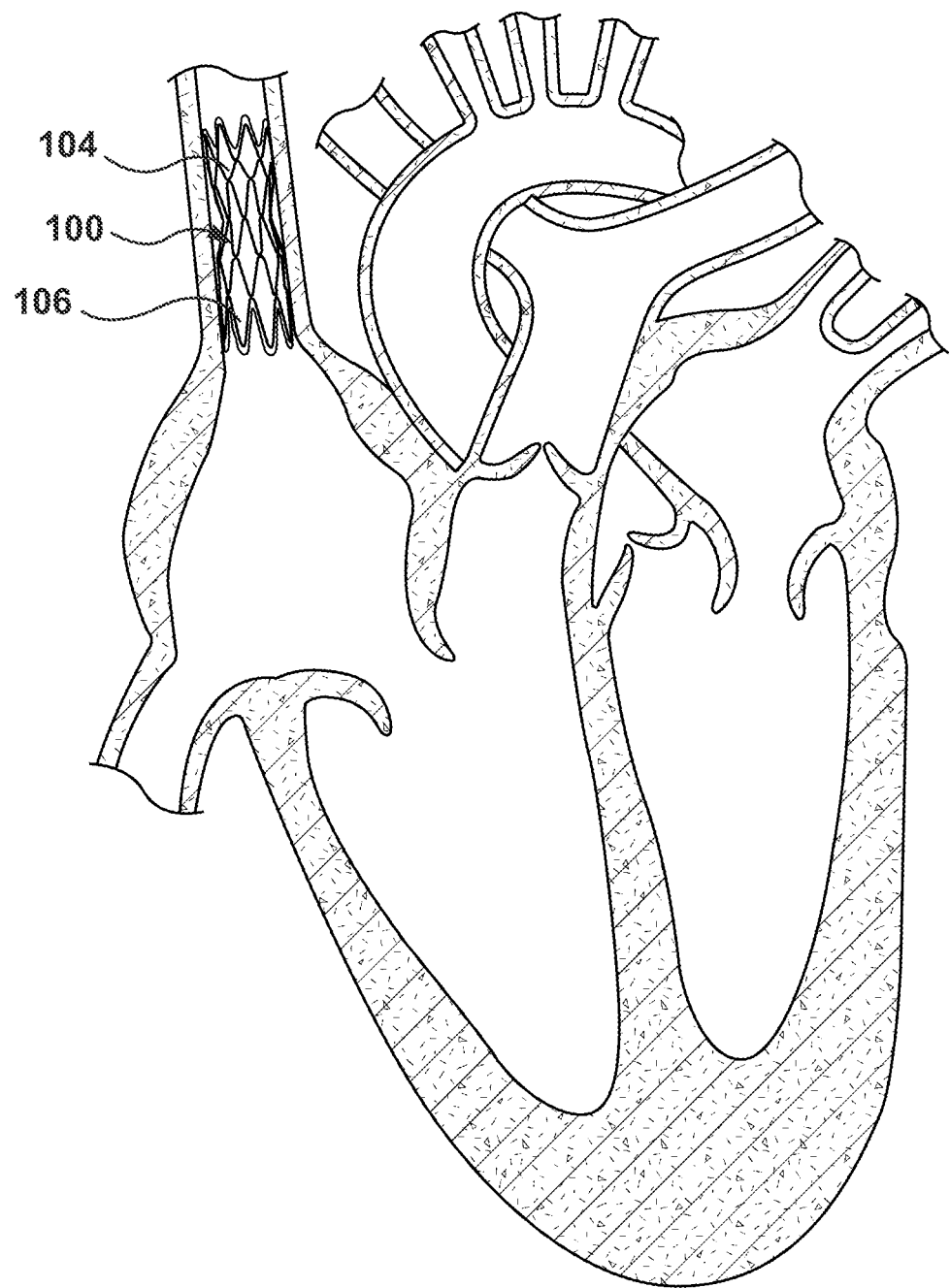
FIG. 4B depicts the prosthetic valve device of FIG. 1 implanted in situ at a treatment site according to another aspect of the present disclosure, wherein the treatment site is a Superior Vena Cava (SVC).

In an embodiment, the prosthetic valve device 100 is an infundibular reducer device configured to be implanted in the pulmonary valve or the infundibulum. FIG. 3 depicts the prosthetic valve device 100 implanted in situ at a treatment site, and the treatment site is a native right ventricular outflow tract (RVOT). In FIG. 3, the native right ventricular outflow tract (RVOT) which includes a native pulmonary valve includes a native pulmonary valve. However, as will be understood by one of ordinary skill in the art, a native right ventricular outflow tract (RVOT) may or may not include a native pulmonary valve. The prosthetic valve device 100 may be used in anatomic locations other than the infundibulum, such as the right ventricular outflow tract and other locations in or near the heart. The purpose of such devices is to allow replacement or prosthetic valves, such as pericardial heart valves, for example, having a smaller diameter than the diameter of the implanted site (e.g., the right ventricular outflow tract) to be implanted. However, other uses of the invention, such as implanting the prosthetic valves described herein at different locations in the body, are contemplated and are not limited to those discussed in the application. For example, the prosthetic valve device 100 may be configured for placement within a different heart valve, i.e., the aortic, mitral, or tricuspid valve, or may be utilized with a prosthetic valve device configured for placement within a venous valve or within other body passageways where it is deemed useful. For example, in another embodiment hereof, the prosthetic valve device 100 is configured to be implanted in the inferior vena cava (IVC) or the superior vena cava (SVC). For example, FIG. 4A depicts the prosthetic valve device 100 implanted in situ at a treatment site and the treatment site is an inferior vena cava (IVC). FIG. 4B depicts the prosthetic valve device 100 implanted in situ at a treatment site and the treatment site is a superior vena cava (SVC). There is no intention to be bound by any expressed or implied theory presented herein.

The backfolding and/or buckling resistant features of the prosthetic valve device 100 will now be described in more detail. As stated above, the outflow end 106 of the frame 102 includes the outflow stent 120B and the second body stent 120D. Backfolding and/or buckling mitigation of the outflow end 106 is an optimization of several features, including the height of each of the outflow stent 120B and the second body stent 120D and the desired outer diameter at the outflow end 106 of the frame 102. More particularly, it has been determined that the desired outer diameter of the outflow end 106, which drives the percentage of patient coverage or eligibility for the prosthetic valve device 100, must be less than a critical diameter calculation. The critical diameter calculation depends on the heights of the outflow stent 120B and the second body stent 120D. In addition, the critical diameter calculation may also depend on dimensions of the delivery system including but not limited to an inner diameter of a capsule or outer sheath of the delivery system. The heights of the stents 120B, 120D can be varied by changing the length of the struts 124B and 124D, or by changing the angle or orientation of the stents 120B and 120D. In an embodiment, the outer diameter OD of the outflow end 106 is between 39 mm and 44 mm, which has been determined to result a high percentage (i.e., at least 70%) of patient coverage or eligibility.

According to an aspect of the present disclosure, the orientation of the outflow end 106 relative to the midportion 105 of the frame 102, as well as the orientation between the outflow stent 120B and the second body stent 120D relative to each other, are particularly configured to resist backfolding and/or buckling during valve deployment. More particularly, as shown in FIG. 1, the second body stent 120D is oriented to extend radially outwards relative to the midportion 105 of the frame 102 in a direction from the first set of crowns 122D thereof to the second set of crowns 126D thereof. The second body stent 120D is oriented at an angle $\theta_1$ which is between 120° and 140° relative to the longitudinal axis $L_A$ of the prosthetic valve device 100. In an embodiment, the angle $\theta_1$ is between 125° and 135° relative to the longitudinal axis $L_A$ of the prosthetic valve device 100. Relative to the fourth body stent 120F, the second body stent 120D is oriented at an angle between 130° and 145°, because the fourth body stent 120F may be parallel to the longitudinal axis $L_A$ or may be angled slightly radially outward in a direction from the first set of crowns 122F thereof to the second set of crowns 126F thereof as described in more detail above.

The outflow stent 120B is oriented at an angle $\theta_{2A}$ which is between 40° and 60° relative to a plane defined by the second body stent 120D. In an embodiment, the angle $\theta_{2A}$ is between 45° and 55° relative to a plane defined by the second body stent 120D. In an embodiment, the outflow stent 120B is oriented at an angle $\theta_{2B}$ which is between 5° and 15° relative to the longitudinal axis $L_A$ of the prosthetic valve device 100. In an embodiment, the angle $\theta_{2B}$ is between 5° and 10° relative to the longitudinal axis $L_A$ of the prosthetic valve device 100. In an embodiment, the angle $\theta_{2B}$ is between −5° and 10° relative to the longitudinal axis $L_A$ of the prosthetic valve device 100. In an embodiment, the outflow stent 120B is substantially parallel to the longitudinal axis $L_A$ of the prosthetic valve device 100 (such that the angle $\theta_{2B}$ is 0°), with "substantially" being defined as a tolerance of 5°. When comparing the corresponding or respective angles of each of the outflow stent 120B and the second body stent 120D relative to the longitudinal axis $L_A$ of the prosthetic valve device 100, notably the angle $\theta_{2B}$ of the outflow stent 120B is less than the corresponding or respective angle of the second body stent 120D, with the corresponding or respective angle of the second body stent 120D being the supplementary angle of angle $\theta_1$ (the supplementary angle of angle $\theta_1$ is labeled as angle $\theta_{1B}$ on FIG. 1). With angle $\theta_1$ being between 120° and 140° relative to the longitudinal axis $L_A$ of the prosthetic valve device 100, the supplementary angle thereof would be between 40° and 60°. Thus, relative to the longitudinal axis $L_A$ of the prosthetic valve device 100, the second body stent 120D flares radially outward to a greater extent or a greater angle than the outflow stent 120B. In an embodiment, the angle $\theta_{2B}$ of the outflow stent is between 5° and 15° relative to the longitudinal axis $L_A$ of the prosthetic valve device 100 while the corresponding or respective acute angle $\theta_{1B}$ of the second body stent 120D is between 40° and 60° relative to the longitudinal axis $L_A$ of the prosthetic valve device 100. In another embodiment, the angle $\theta_{2B}$ of the outflow stent is between 5° and 10° relative to the longitudinal axis $L_A$ of the prosthetic valve device 100 while the corresponding or respective acute angle $\theta_{1B}$ of the second body stent 120D is between 45° and 55° relative to the longitudinal axis $L_A$ of the prosthetic valve device 100. In another embodiment, the angle $\theta_{2B}$ of the outflow stent is between −5° and 10° relative to the longitudinal axis $L_A$ of the prosthetic valve device 100 while the corresponding or respective acute angle $\theta_{1B}$ of the second body stent 120D is between 45° and 55° relative to the longitudinal axis $L_A$ of the prosthetic valve device 100. In another embodiment, the angle $\theta_{2B}$ of the outflow stent is substantially 0° relative to the longitudinal axis $L_A$ of the prosthetic valve device 100 while the corresponding or respective acute angle $\theta_{1B}$ of the second body stent 120D is between 45° and 55° relative to the longitudinal axis $L_A$ of the prosthetic valve device 100.

The resulting relationship and orientation between the outflow stent 120B and the second body stent 120D relative to each other is particularly configured to resist backfolding and/or buckling during valve deployment, and is achieved by initially forming the outflow stent 120B in a tapered or reverse orientation relative to the second body stent 120D. The initial reverse or opposing orientation of the outflow stent 120B (i.e., tapered and extending radially inwards) relative to the orientation of the second body stent 120D (i.e., flared and extending radially outwards) configures the outflow end 106 of the frame 102 to be particularly resistant to backfolding, because the initial reverse orientation of the outflow stent 120B controls the energy release of the outflow stent 120B and second body stent 120D to mitigate or avoid backfolding thereof.

Figure 5:
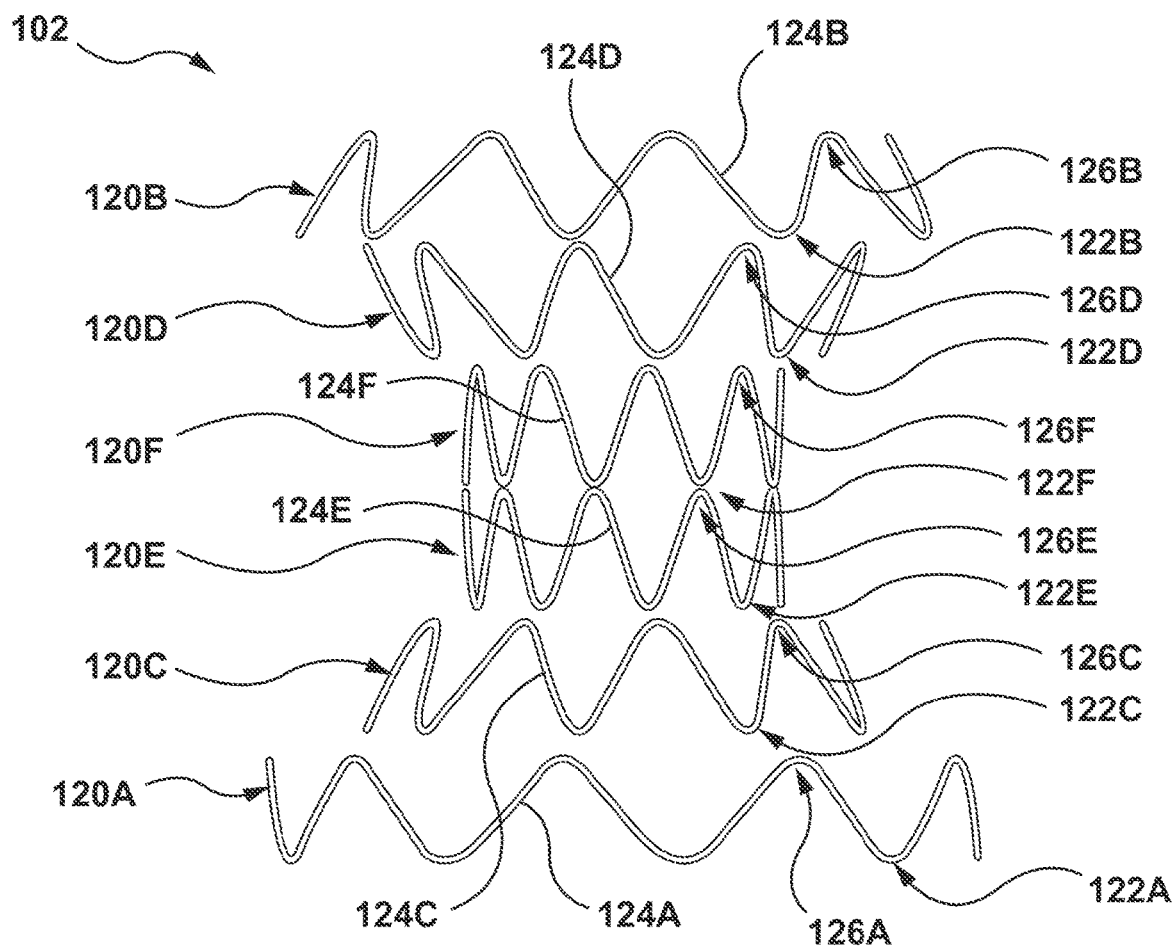
FIG. 5 is a side exploded view of an inflow stent, an outflow stent, and a plurality of body stents of the prosthetic valve device of FIG. 1.
Figures 6A, 6B:
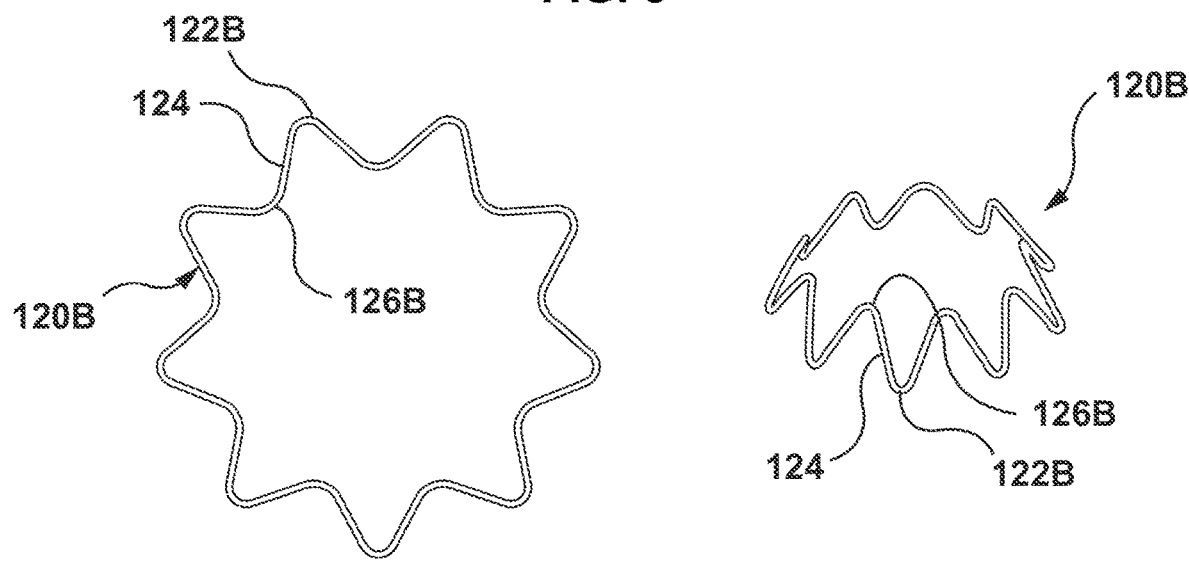
FIG. 6A is a top view of the outflow stent of FIG. 5.
FIG. 6B is a perspective view of the outflow stent of FIG. 5.
Figure 7A:
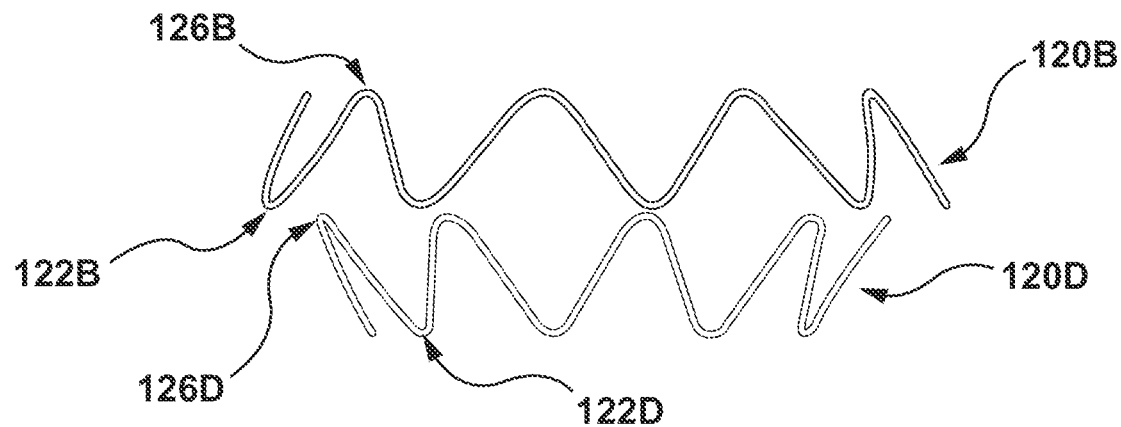
FIG. 7A is a side view of the outflow stent and a body stent adjacent to the outflow stent of FIG. 5, wherein the stents are depicted in their radially expanded or deployed configurations prior to being attached to a tubular graft of the prosthetic valve device.
Figure 7B:
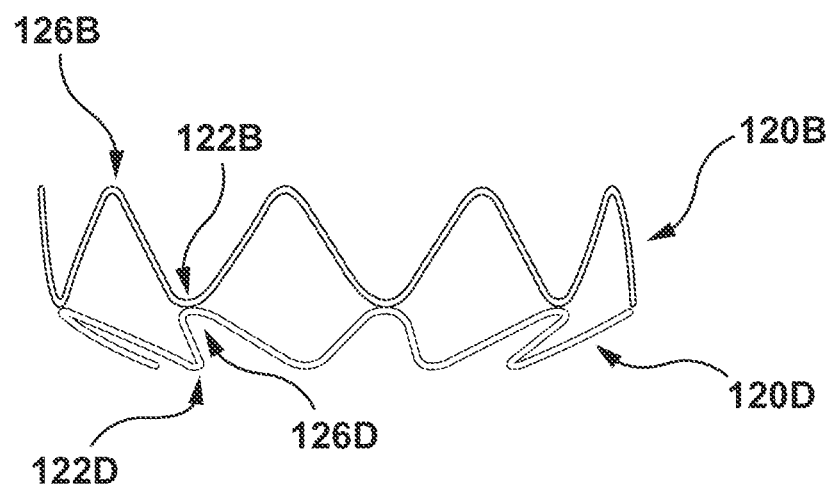
FIG. 7B is a side view of the outflow stent and a body stent adjacent to the outflow stent of FIG. 5, wherein the stents are depicted in their radially expanded or deployed configurations after being attached to a tubular graft of the prosthetic valve device.
Figure 8:
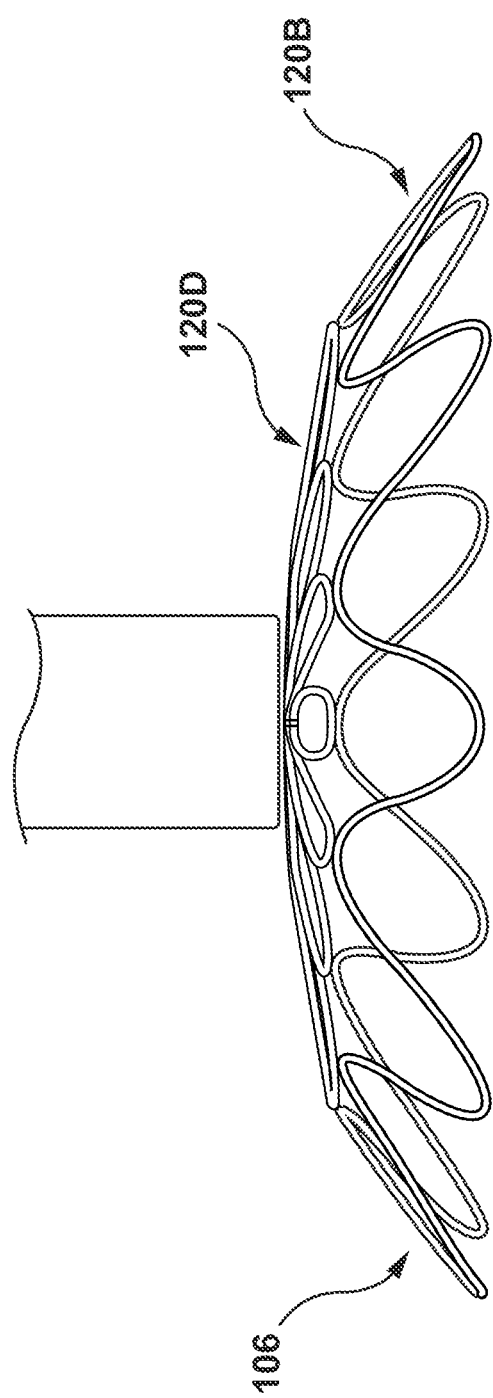
FIG. 8 is a side view of an outflow end of the prosthetic valve device of FIG. 1 being deployed from a distal end of a delivery device.

More particularly, as will be described with reference to FIGS. 5-8, prior to attachment to the tubular graft 110 the outflow stent 120B is oriented to extend radially inwards in a direction from the first set of crowns 122B thereof to the second set of crowns 126B thereof. However, after attachment to the tubular graft 110 and the second body stent 120D as shown in FIG. 1 and described above, the outflow stent 120B is oriented to extend substantially parallel to the longitudinal axis of the prosthesis or radially outwards relative to the longitudinal axis of the prosthesis in a direction from the first set of crowns 122B thereof to the second set of crowns 126B thereof. FIG. 5 is a side exploded view of the frame 102 and depicts a side view of each of the inflow stent 120A, the outflow stent 120B, and the plurality of body stents 120C, 120D, 120E, 120F of the prosthetic valve device 100 in their radially expanded or deployed configuration prior to assembly, i.e., prior to attachment to the tubular graft 110 and attachment to each other. FIG. 6A and FIG. 6B are top and perspective views, respectively, of the outflow stent 120B prior to assembly. FIGS. 7A and 7B are side views of the outflow stent 120B and the second body stent 120D. In FIG. 7A, the outflow stent 120B and the second body stent 120D are depicted in their radially expanded or deployed configurations prior to attachment to the tubular graft 110. In FIG. 7B, the outflow stent 120B and the second body stent 120D are depicted in their radially expanded or deployed configurations after being attached to the tubular graft 110 of the prosthetic valve device 100. FIG. 8 is a side view of the outflow end 106 of the frame 102 (which includes the outflow stent 120B and the second body stent 120D) of the prosthetic valve device 100 being deployed from a distal end of a delivery device, with no backfolding or buckling of the outflow end 106 occurring.

The behavior or relationship between the outflow stent 120B and the second body stent 120D prior to and after attachment to the tubular graft 110 is best shown in FIGS. 7A and 7B. In FIG. 7A, the outflow stent 120B and the second body stent 120D are depicted in their radially expanded or deployed configurations, prior to attachment to the tubular graft 110. Each of the outflow stent 120B and the second body stent 120D is manufactured or formed in its radially expanded or deployed configurations, so FIG. 7A depicts each of the outflow stent 120B and the second body stent 120D is its as-formed configuration. As shown, the outflow stent 120B is formed with the unconstrained diameter of the first set of crowns 122B being greater than the unconstrained diameter of the second set of crowns 126B and the second body stent 120D is formed with the unconstrained diameter of the first set of crowns 122D being less than the unconstrained diameter of the second set of crowns 126D. In addition, as initially formed, the unconstrained diameter of the first set of crowns 122B of the outflow stent 120B is greater than the unconstrained diameter of the second set of crowns 126D of the second body stent 120D. In an embodiment, the unconstrained diameter of the first set of crowns 122B of the outflow stent 120B is between 15 and 20% greater than the unconstrained diameter second set of crowns 126D of the second body stent 120D. For example, in an embodiment, the outflow stent 120B is formed with a diameter of 50 mm at the first set of crowns 122B while the second body stent 120D is formed with a diameter of 41 mm at the second set of crowns 126D. Further, the outflow stent 120B is formed with a diameter of 40.5 mm at the second set of crowns 126B and the second body stent 120D is formed with a diameter of 31 mm at the first set of crowns 122D. Prior to attachment to the tubular graft 110, the outflow stent 120B is oriented to extend radially inwards in a direction from the first set of crowns 122B thereof to the second set of crowns 126B thereof at an angle between 20° and 35° relative to the longitudinal axis $L_A$ of the prosthetic valve device. Prior to attachment to the tubular graft 110, the second body stent 120D is oriented to extend radially outwards in a direction from the first set of crowns 122D thereof to the second set of crowns 126D thereof at an angle between 20° and 35° relative to the longitudinal axis $L_A$ of the prosthetic valve device.

In FIG. 7B, the outflow stent 120B and the second body stent 120D are depicted in their radially expanded or deployed configurations after being attached to the tubular graft 110 of the prosthetic valve device 100 (although the tubular graft 110 is omitted for sake of clarity) and attached to each other. Due to the attachment to the second set of crowns 126D and the attachment to the tubular graft 110, the first set of crowns 122B of the outflow stent 120B is slightly radially constrained relative to the configuration of FIG. 7A. With additional reference to FIG. 8, which depicts the outflow end 106 being deployed from a distal end portion of a delivery catheter, the outflow stent 120B is deployed or released from the delivery catheter prior to the second body stent 120D. Since the first set of crowns 122B of the outflow stent 120B is slightly radially constrained due to attachment to the second body stent 120D and the tubular graft 110, the energy release of the outflow stent 120B is controlled or reduced such that backfolding of the outflow stent 120B is prevented.

The inflow end 104 of the frame 102 is also optimized to mitigate against backfolding thereof. The inflow end 104 includes the inflow stent 120A and the first body stent 120C. The orientation of the inflow end 104 relative to the midportion 105, as well as the orientation between the inflow stent 120A and the first body stent 120C relative to each other, are particularly configured to resist backfolding and/or buckling during valve deployment. More particularly, the first body stent 120C is oriented to extend radially outwards relative to the midportion 105 of the frame 102 in a direction from the second set of crowns 126C thereof to the first set of crowns 122C thereof. The first body stent 120C is oriented at an angle $\theta_3$ which is between 120° and 140° relative to the longitudinal axis $L_A$ of the prosthetic valve device 100. In an embodiment, the angle $\theta_3$ is between 125° and 135° relative to the longitudinal axis $L_A$ of the prosthetic valve device 100. Relative to the third body stent 120E, the first body stent 120C is oriented at an angle between 130° and 145°, because the third body stent 120E may be parallel to the longitudinal axis $L_A$ or may be angled slightly radially outward in a direction from the second set of crowns 126E thereof to the first set of crowns 122E thereof as described in more detail above. The inflow stent 120A is oriented to extend radially outwards in a direction from the second set of crowns 126A thereof to the first set of crowns 122A thereof. The inflow stent 120A is oriented at an angle $\theta_4$ which is between 10° and 30° relative to a plane defined by the first body stent 120C. In an embodiment, the angle $\theta_4$ is between 15° and 25° relative to a plane defined by the first body stent 120C.

It has been determined that increasing the diameters of the wires that form particular stents 120 further optimizes resistance to backfolding and/or buckling of the prosthetic valve device 100. Particularly, according to an embodiment hereof, each of the first body stent 120C, the second body stent 120D, and the outflow stent 120B is formed by a wire having a first diameter that is greater than a second diameter of the remaining stents of the prosthetic valve device 100, i.e., the inflow stent 120A, the third body stent 120E, and the fourth body stent 120F. The first diameter is between 5% and 10% greater than the second diameter. In an embodiment, the first diameter of the first body stent 120C, the second body stent 120D, and the outflow stent 120B is 0.015 inches while the second diameter of the inflow stent 120A and the third and fourth body stents 120E, 120F is 0.014 inches. In addition to contributing to the optimal mitigation of backfolding and/or buckling, the increased wire diameter of the first body stent 120C, the second body stent 120D, and the outflow stent 120B also increase visibility of the prosthetic valve device 100 because the larger diameter wires are more visible under fluoroscopy. While other characteristics and/or geometry of the stents 120 may be varied to improve resistance to backfolding and/or buckling, such as the height of the struts 124, increasing the wire diameter of the particular combination of the first body stent 120C, the second body stent 120D, and the outflow stent 120B has been found to improve buckling resistance without causing an increase in strain within the struts. If the height of select struts 124 is shortened to increase strength of the corresponding stent, an increase in strain also occurs and the fatigue life of the prosthetic valve device 100 may be undesirably lower.

Further optimization of the prosthetic valve device 100 to mitigate against backfolding and/or buckling thereof also includes reinforcing the connections between at least one pair of adjacent stents 120. More particularly, with respect to the prosthetic valve device 100 of FIG. 1, each pair of adjacent stents 120 of the frame 102 are attached to each other in a crown-to-crown configuration. The second set of crowns 126A, 126C, 126D, 126E, 126F of each of the inflow stent 120A and each body stent of the plurality of body stents 120C, 120D, 120E, 120F is disposed against and attached to the first set of crowns of the stent directly adjacent thereto. More particularly, the second set of crowns 126A, 126C, 126D, 126E, 126F of each of the inflow stent 120A and each body stent of the plurality of body stents 120C, 120D, 120E, 120F is attached to the first set of crowns of an adjacent stent via stitching. Each pair of adjacent stents 120 are attached to each other with at least one or more stitches that extend over the abutting crowns, in an axial direction. The second set of crowns 126A of the inflow stent 120A is attached to the first set of crowns 122C of the first body stent 120C, the second set of crowns 126C of the first body stent 120C is attached to the first set of crowns 122E of the third body stent 120E, the second set of crowns 126E of the third body stent 120E is attached to the first set of crowns 122F of the fourth body stent 120F, the second set of crowns 126F of the fourth body stent 120F is attached to the first set of crowns 122D of the second body stent 120D, and the second set of crowns 126D of the second body stent 120D is attached to the first set of crowns 122B of the outflow stent 120B.

Figure 9:
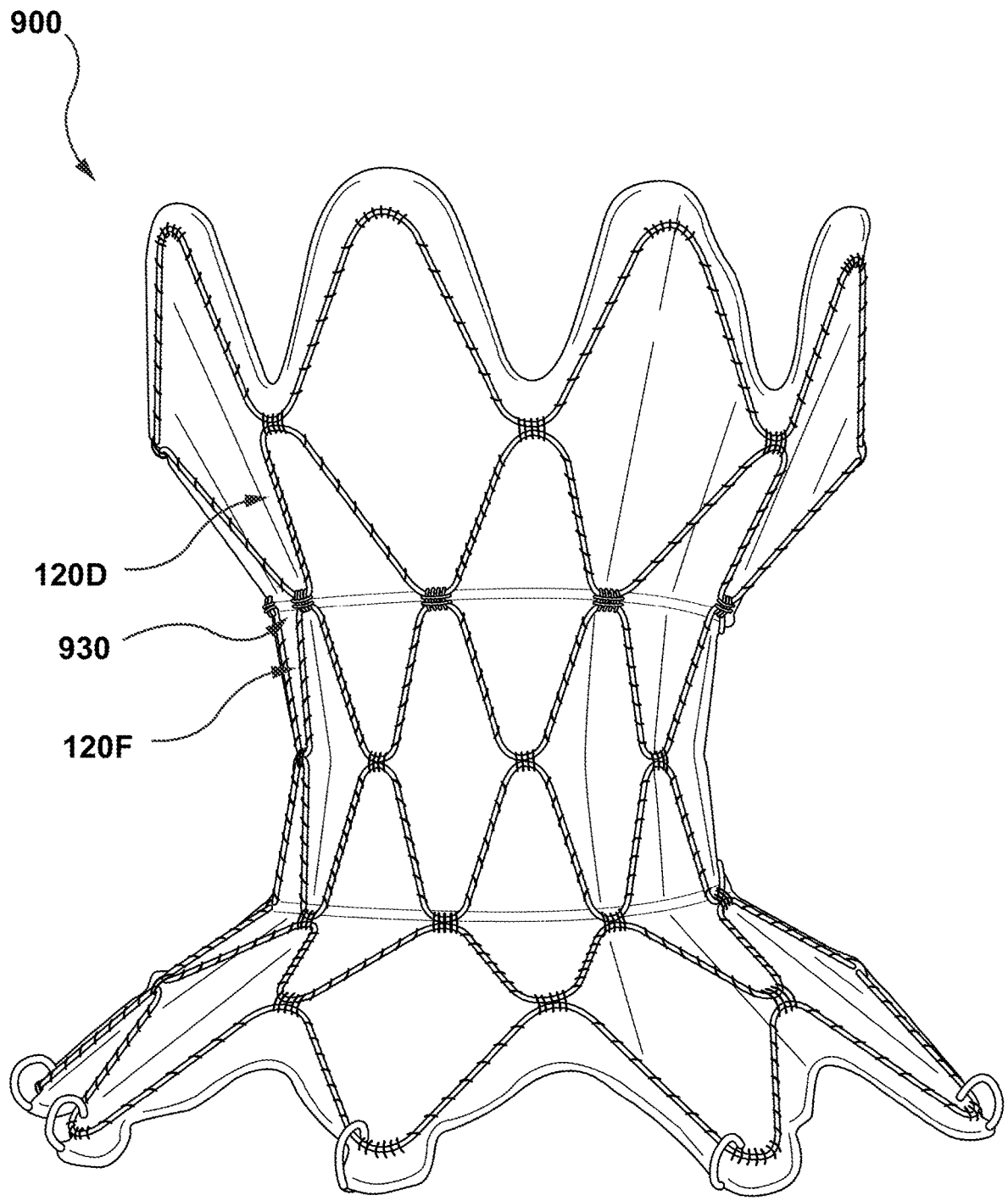
FIG. 9 is a side view of a prosthetic valve device according to an aspect of the present disclosure, wherein the prosthetic valve device includes a reinforced connection at a plurality of crown to crown connections of the prosthetic valve device.
Figure 10:
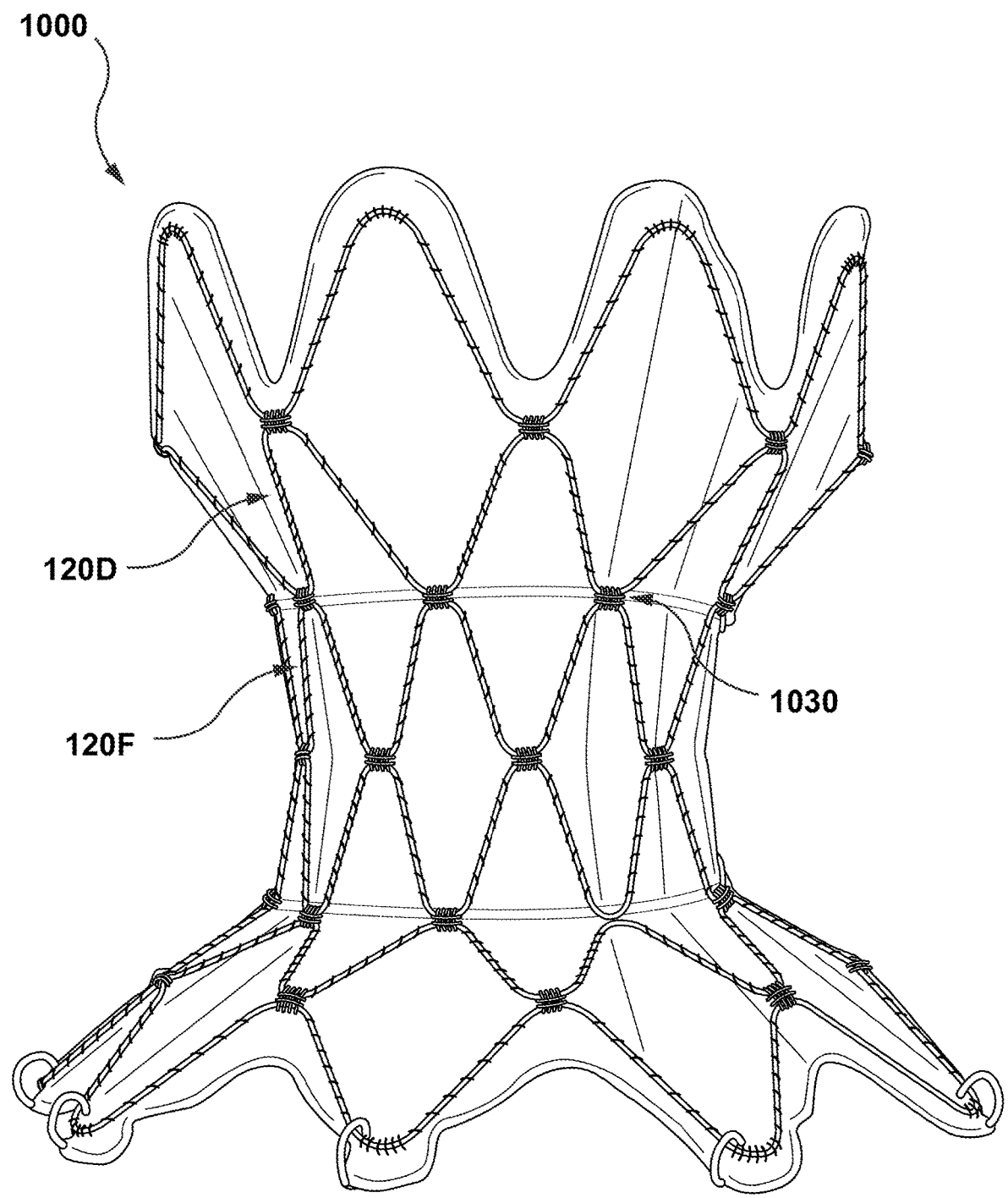
FIG. 10 is a side view of a prosthetic valve device according to an aspect of the present disclosure, wherein the prosthetic valve device includes a reinforced connections at every crown to crown connection of the prosthetic valve device.

With reference to FIG. 9, in order to further mitigate against backfolding and/or buckling, according to another aspect of the present disclosure a reinforced connection 930 is utilized at least between the abutting crowns between the second body stent 120D and the fourth body stent 120F of a prosthetic valve device 900. The prosthetic valve device 900 is the same as the prosthetic valve device 100 except for the addition of the reinforced connections 930. The abutting crowns between the second body stent 120D and the fourth body stent 120F include the second set of crowns 126F of the fourth body stent 120F and the first set of crowns 122D of the second body stent 120D.

Figure 11:
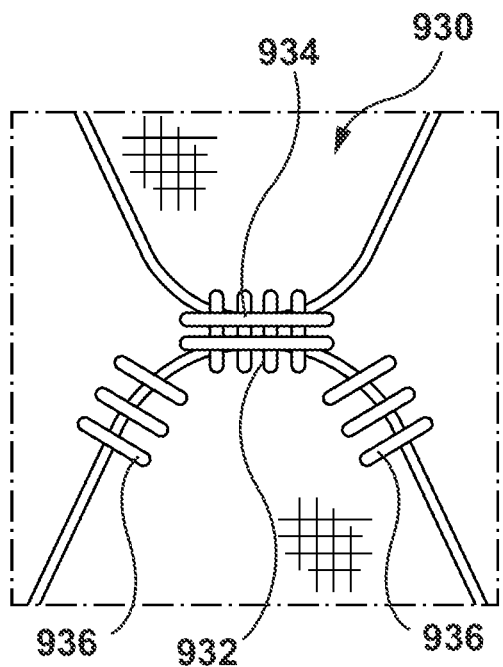
FIG. 11 is a side view of a reinforced connection according to an aspect of the present disclosure.

An enlarged view of the reinforced connection 930 is shown in FIG. 11. The reinforced connection 930 includes a plurality of axial suture loops 932 that extend over the abutting crowns between the second body stent 120D and the fourth body stent 120F in an axial direction as well as a plurality of transverse suture loops 934 that extend over the plurality of axial suture loops 932 in a direction transverse to the axial suture loops 932. Each transverse loop 934 is perpendicular to the axial suture loops 932, which extend substantially parallel to the longitudinal axis $L_A$ of the prosthetic valve device 900. The transverse suture loops 934 are configured to prevent adjacent stents 120D, 120F from moving and rotating against each other. Reinforced connection 930 effectively creates a pin joint that permits limited rotation or radial movement between adjacent stents 120D, 120F but prevents sliding or side-to-side movement between adjacent stents 120D, 120F. As a result, reinforced connection 930 further mitigate buckling and migration at critical areas of the prosthetic valve device 900. In addition, there is less manufacturing variability in the prosthetic valve device 900 due to the reinforced connections because the transverse suture loops 934 lessen the need for precise placement of the axial suture loops 932.

Figure 12:
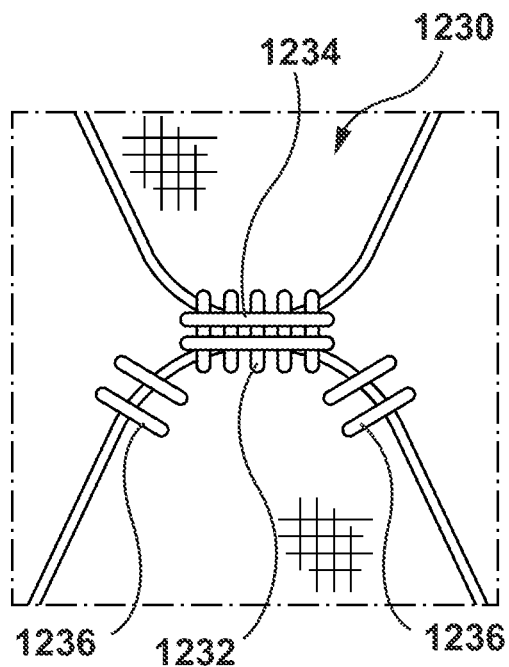
FIG. 12 is a side view of a reinforced connection according to another aspect of the present disclosure.
Figure 13:
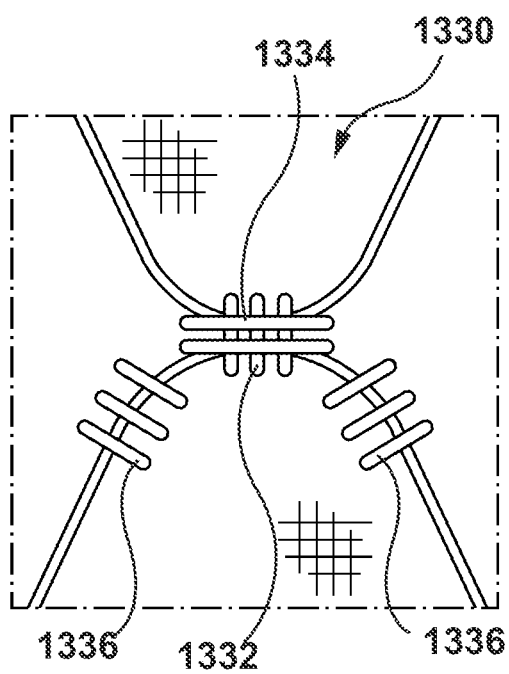
FIG. 13 is a side view of a reinforced connection according to another aspect of the present disclosure.

In the embodiment of FIGS. 9 and 11, each reinforced connection 930 includes exactly four axial suture loops 932 and two transverse suture loops 934. Three stitches 936 are disposed on each side of the reinforced connection 930. It has been found that two transverse suture loops is an optimal number of loops for the reinforced connection because two transverse suture loops provide the desired result while not causing packing or profile concerns. Particularly, while a greater number of transverse suture loops may be utilized, the higher number of transverse suture loops may undesirably increase the packing profile of the prosthetic valve device 900 when crimped. However, the configuration of the reinforced connection 930 is exemplary and other configurations are contemplated. In the embodiment of FIG. 12, each reinforced connection 1230 includes exactly five axial suture loops 1232 and two transverse suture loops 1234. Two stitches 1236 are disposed on each side of the reinforced connection 1230. In the embodiment of FIG. 13, each reinforced connection 1330 includes exactly three axial suture loops 1332 and two transverse suture loops 1334.

Figure 14:
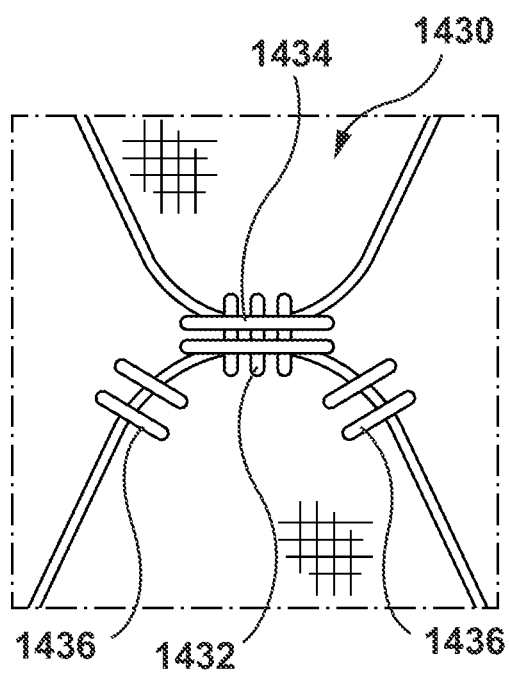
FIG. 14 is a side view of a reinforced connection according to another aspect of the present disclosure.

Three stitches 1336 are disposed on each side of the reinforced connection 1330. In the embodiment of FIG. 14, each reinforced connection 1430 includes exactly three axial suture loops 1432 and two transverse suture loops 1434. Two stitches 1436 are disposed on each side of the reinforced connection 1430.

Although the embodiment of FIG. 9 depicts reinforced connections 930 between the abutting crowns between the second body stent 120D and the fourth body stent 120F, other embodiments are contemplated. Particularly, in the embodiment of FIG. 10, reinforced connections 1030 are utilized at every crown-to-crown connection of a prosthetic valve device 1000. Having the reinforced connections 1030 on every crown-to-crown connection further reduces buckling throughout the length of the prosthetic valve device 1000 and does not adversely affect the packing profile of the prosthetic valve device 1000 when crimped. Other embodiments are contemplated herein, and it will be understood that it is not required for every crown-to-crown connection of the prosthetic valve device 1000 to include a reinforced connection.

Figure 15:
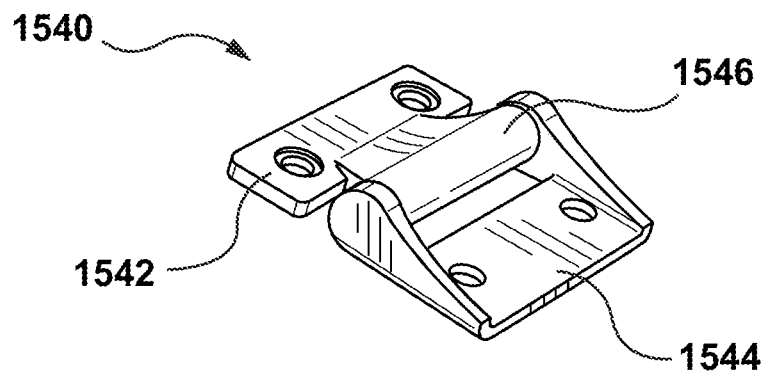
FIG. 15 is a perspective view of a hinge component according to an aspect of the present disclosure.
Figure 16:
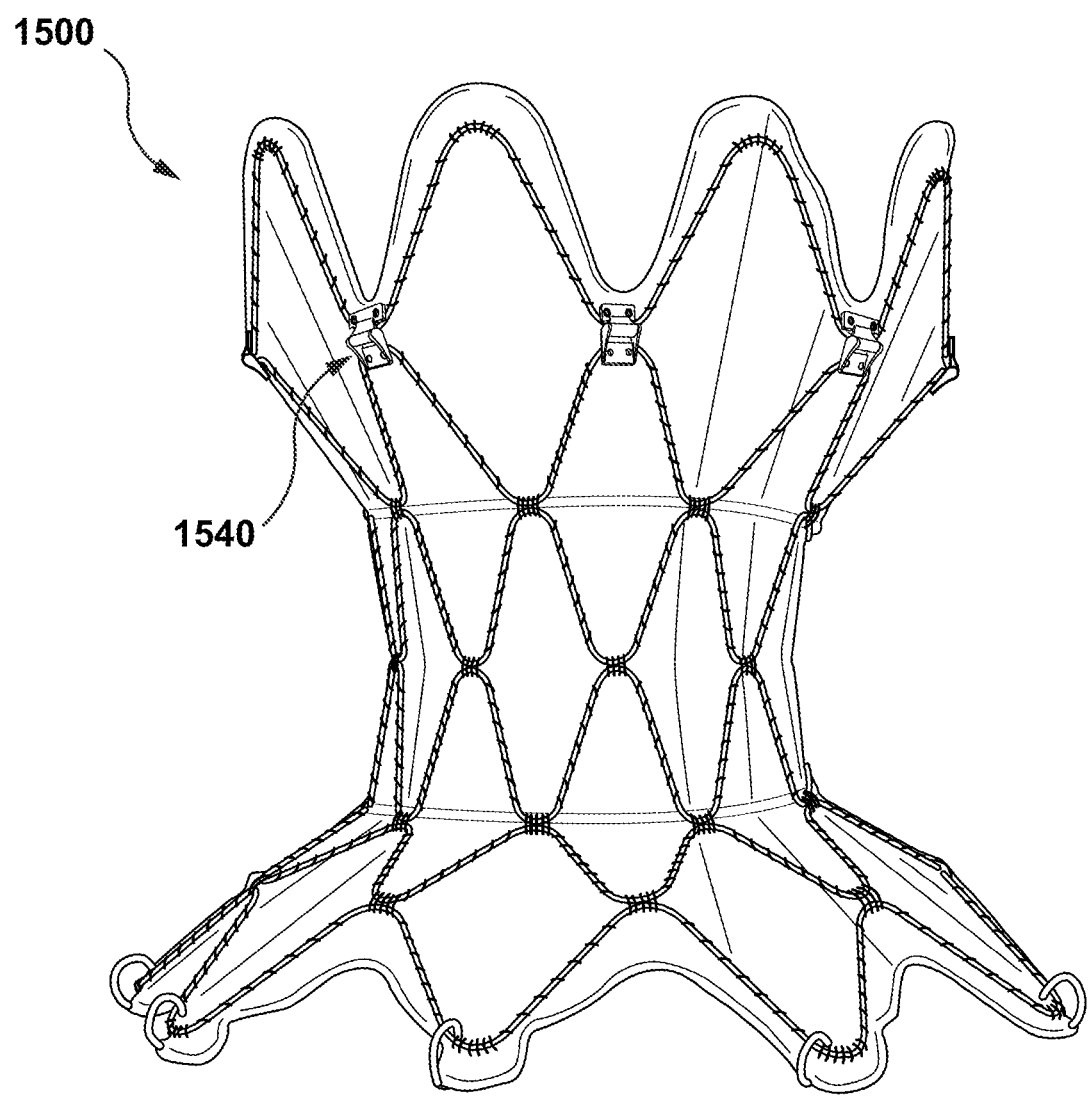
FIG. 16 is a side view of a prosthetic valve device according to an aspect of the present disclosure, wherein the prosthetic valve device includes the hinge component at a plurality of crown to crown connections of the prosthetic valve device.

Turning now to FIGS. 15-16, according to another aspect of the present disclosure, a hinge component 1540 may be utilized as an alternative reinforced connection between the outflow stent 120B and the second body stent 120D at the outflow end 106 of the frame 102. FIG. 15 is a perspective view of the hinge component 1540, and FIG. 16 is a side view of a prosthetic valve device 1500 including the hinge component 1540 at a plurality of crown to crown connections thereof. Particularly, each crown of the second set of crowns 126D of the second body stent 120D is attached to a respective or abutting crown of the first set of crowns 122B of the outflow stent 120B with a hinge component 1540. Each hinge component 1540 includes a first body plate 1542 connected to a second body plate 1544 via a hinge 1546. The hinge 1546 permits limited rotation or radial movement between the first and second body plates 1542, 1544 but prevents sliding or side-to-side movement between the first and second body plates 1542, 1544. When utilized as the connection mechanism between the outflow stent 120B and the second body stent 120D, the first body plate 1542 is attached to a crown of the first set of crowns 122B of the the outflow stent 120B and the second body plate 1544 is attached to a crown of the second set of crowns 126D of the second body stent 120D. The hinge 1546 then permits limited rotation or radial movement between the stents 120B, 120D but prevents sliding or side-to-side movement between the stents 120B, 120D. The hinge 1546 is configured to control or prevent over rotation between the stents 120B, 120D.

Each hinge component 1540 is formed from a radiopaque material in order to aid in placement of a prosthetic valve device 1500 at the target landing zone. Particularly, the hinge components 1540 would effectively be a ring of radiopaque markers within the outflow end 106 of the prosthetic valve device 1500 to provide a radiopaque landing zone for implantation.

Embodiments hereof also relate to a method of manufacturing the prosthetic valve device 100. The method of manufacturing the prosthetic valve device 100 includes forming or constructing each of the inflow stent 120A, the outflow stent 120B, and each stent of the plurality of body stents 120C, 120D, 120E, 120F as an independent sinusoidal patterned radially-expandable ring in its radially expanded or deployed configuration. FIG. 5 described herein depicts each of the inflow stent 120A, the outflow stent 120B, and each stent of the plurality of body stents 120C, 120D, 120E, 120F in their radially expanded or deployed configuration prior to assembly, i.e., prior to attachment to the tubular graft 110 and attachment to each other. As explained above with reference to FIG. 7A, prior to attachment to the tubular graft 110, the outflow stent 120B is oriented to extend radially inwards in a direction from the first set of crowns 122B thereof to the second set of crowns 126B thereof. More particularly, prior to attachment to the tubular graft 110, the outflow stent 120B is oriented to extend radially inwards in a direction from the first set of crowns 122B thereof to the second set of crowns 126B thereof at an angle between 20° and 35° relative to the longitudinal axis $L_A$ of the prosthetic valve device. Prior to attachment to the tubular graft 110, the second body stent 120D is oriented to extend radially outwards in a direction from the first set of crowns 122D thereof to the second set of crowns 126D thereof at an angle between 20° and 35° relative to the longitudinal axis $L_A$ of the prosthetic valve device. The initial reverse or opposing orientation of the outflow stent 120B (i.e., tapered and extending radially inwards) relative to the orientation of the second body stent 120D (i.e., flared and extending radially outwards) configures the outflow end 106 of the frame 102 to be particularly resistant to backfolding, because the initial reverse orientation of the outflow stent 120B controls the energy release of the outflow stent 120B and second body stent 120D to mitigate or avoid backfolding thereof.

The method of manufacturing the prosthetic valve device 100 further includes attaching each of the inflow stent 120A, the outflow stent 120B, and each stent of the plurality of body stents 120C, 120D, 120E, 120F to the tubular graft 110 via stitching. As described above with respect to FIG. 1 and FIG. 7B, after being attached to the tubular graft 110, the outflow stent 120B is oriented to extend substantially parallel to the longitudinal axis of the prosthesis or radially outwards relative to the longitudinal axis of the prosthesis in a direction from the first set of crowns 122B thereof to the second set of crowns 126B thereof. The outflow stent 120B is oriented at the angle $\theta_{2A}$ (shown on FIG. 1) between 40° and 60° relative to a plane defined by the second body stent 120D. In an embodiment, the angle $\theta_{2A}$ is between 45° and 55°. After attachment to the tubular graft 110, the second body stent 120D is oriented to extend radially outwards relative to the midportion 105 of the frame 102 in a direction from the first set of crowns 122D thereof to the second set of crowns 126D thereof. The second body stent 120D is oriented at an angle $\theta_1$ (shown on FIG. 1) between 120° and 140° relative to the longitudinal axis $L_A$ of the prosthetic valve device 100. In an embodiment, the angle $\theta_1$ is between 125° and 135°. Relative to the fourth body stent 120F, the second body stent 120D is oriented at an angle between 130° and 145°. Notably, after being attached to the tubular graft 110, the outflow stent 120B is oriented at an angle $\theta_{2B}$ (shown on FIG. 1) relative to the longitudinal axis $L_A$ of the prosthetic valve device 100. When comparing the corresponding or respective angles of each of the outflow stent 120B and the second body stent 120D relative to the longitudinal axis $L_A$ of the prosthetic valve device 100, the angle $\theta_{2B}$ of the outflow stent 120B is less than the corresponding or respective angle of the second body stent 120D, with the corresponding or respective angle of the second body stent 120D being the supplementary angle of angle $\theta_1$.

The method of manufacturing the prosthetic valve device 100 further includes attaching each pair of adjacent stents 120 of the frame 102 to each other in a crown-to-crown configuration. The second set of crowns 126A, 126C, 126D, 126E, 126F of each of the inflow stent 120A and each body stent of the plurality of body stents 120C, 120D, 120E, 120F is disposed against and attached to the first set of crowns of the stent directly adjacent thereto as described herein. Each pair of adjacent stents 120 are attached to each other with a plurality of axial stitches that extend over the abutting crowns, in an axial direction. In addition, to further mitigate against backfolding and/or buckling, one or more of the crown-to-crown connections may be reinforced with the addition of at least two transverse sutures as described above with respect to FIGS. 9-14.

The method of manufacturing the prosthetic valve device 100 further includes attaching the prosthetic valve component 108 to the tubular graft 110 and/or the frame 102. The step of attaching the prosthetic valve component 108 may occur before or after the assembly of the stents 120 to the tubular graft 110.

The foregoing description has been presented for purposes of illustration and enablement and is not intended to be exhaustive or to limit the invention to the precise form disclosed. Other modifications and variations are possible in light of the above teachings. The embodiments and examples were chosen and described in order to best explain the principles of the invention and its practical application and to thereby enable others skilled in the art to best utilize the invention in various embodiments and various modifications as are suited to the particular use contemplated. It is intended that the appended claims be construed to include other alternative embodiments of the invention.

What is claimed is:

1. A prosthesis for implantation within a body lumen, the prosthesis having a radially expanded configuration and a radially compressed configuration, the prosthesis comprising:
    a tubular graft defining a lumen that extends from an inflow end to an outflow end thereof, wherein a longitudinal axis of the prosthesis is defined by the lumen of the tubular graft;
    a prosthetic valve component disposed within the lumen of the tubular graft;
    an inflow stent attached to the inflow end of the tubular graft;
    an outflow stent attached to the outflow end of the tubular graft; and
    a plurality of body stents attached to the tubular graft and disposed between the inflow stent and the outflow stent, a first body stent of the plurality of body stents being disposed directly adjacent to the inflow stent and a second body stent of the plurality of body stents being disposed directly adjacent to the outflow stent,
    wherein each of the inflow stent, the outflow stent, and each stent of the plurality of body stents is a sinusoidal patterned radially-expandable ring having a first set of crowns and a second set of crowns, the first set of crowns being disposed closer to the inflow end of the tubular graft than the second set of crowns, and
    wherein the second set of crowns of each of the inflow stent and each body stent of the plurality of body stents is disposed against and attached to the first set of crowns of an adjacent stent, and
    wherein the second body stent is oriented to extend radially outwards in a direction from the first set of crowns thereof to the second set of crowns thereof, the second body stent being oriented at a first acute angle relative to the longitudinal axis of the prosthesis, and
    wherein the outflow stent is oriented substantially parallel relative to the longitudinal axis of the prosthesis, and
    wherein each of the first body stent, the second body stent, and the outflow stent is formed by a wire having a first diameter that is greater than a wire having a second diameter of the remaining body stents of the prosthesis.

2. The prosthesis of claim 1, wherein the outflow stent is oriented at an angle between 40° and 60° relative to the second body stent.

3. The prosthesis of claim 1, wherein the first body stent is oriented to extend radially outwards in a direction from the second set of crowns thereof to the first set of crowns thereof and the first body stent is oriented at an angle between 120° and 140° relative to the longitudinal axis of the prosthesis.

4. The prosthesis of claim 1, wherein the plurality of body stents includes a third body stent and a fourth body stent disposed between the first and second body stents, the third and fourth body stents being oriented to extend substantially parallel to the longitudinal axis of the prosthesis.

5. The prosthesis of claim 1, wherein the first diameter is between 5% and 10% greater than the second diameter.

6. The prosthesis of claim 1, wherein the plurality of body stents includes a third body stent and a fourth body stent disposed between the first and second body stents, and
    wherein the second set of crowns of the inflow stent is attached to the first set of crowns of the first body stent, and
    wherein the second set of crowns of the first body stent is attached to the first set of crowns of the third body stent, and
    wherein the second set of crowns of the third body stent is attached to the first set of crowns of the fourth body stent, and
    wherein the second set of crowns of the fourth body stent is attached to the first set of crowns of the second body stent, and
    wherein the second set of crowns of the second body stent is attached to the first set of crowns of the outflow stent.

7. The prosthesis of claim 6, wherein the second set of crowns of the inflow stent is attached to the first set of crowns of the first body stent by a reinforced connection including at least two axial suture loops extending over adjacent crowns and at least two transverse suture loops extending over the at least two axial suture loops, and
    wherein the second set of crowns of the first body stent is attached to the first set of crowns of the third body stent by a reinforced connection including at least two axial suture loops extending over adjacent crowns and at least two transverse suture loops extending over the at least two axial suture loops, and
    wherein the second set of crowns of the third body stent is attached to the first set of crowns of the fourth body stent by a reinforced connection including at least two axial suture loops extending over adjacent crowns and at least two transverse suture loops extending over the at least two axial suture loops, and
    wherein the second set of crowns of the fourth body stent is attached to the first set of crowns of the second body stent by a reinforced connection including at least two axial suture loops extending over adjacent crowns and at least two transverse suture loops extending over the at least two axial suture loops, and
    wherein the second set of crowns of the second body stent is attached to the first set of crowns of the outflow stent by a reinforced connection including at least two axial suture loops extending over adjacent crowns and at least two transverse suture loops extending over the at least two axial suture loops.

8. The prosthesis of claim 7, wherein the second set of crowns of the inflow stent is attached to the first set of crowns of the first body stent by a reinforced connection including exactly three axial suture loops extending over adjacent crowns and exactly two transverse suture loops extending over the three axial suture loops, and wherein the second set of crowns of the first body stent is attached to the first set of crowns of the third body stent by a reinforced connection including exactly three axial suture loops extending over adjacent crowns and exactly two transverse suture loops extending over the three axial suture loops, and wherein the second set of crowns of the third body stent is attached to the first set of crowns of the fourth body stent by a reinforced connection including exactly three axial suture loops extending over adjacent crowns and exactly two transverse suture loops extending over the three axial suture loops, and wherein the second set of crowns of the fourth body stent is attached to the first set of crowns of the second body stent by a reinforced connection including exactly three axial suture loops extending over adjacent crowns and exactly two transverse suture loops extending over the three axial suture loops, and wherein the second set of crowns of the second body stent is attached to the first set of crowns of the outflow stent by a reinforced connection including exactly three axial suture loops extending over adjacent crowns and exactly two transverse suture loops extending over the three axial suture loops.

9. The prosthesis of claim 1, wherein the tubular graft is formed from a knit fabric.

10. The prosthesis of claim 1, wherein the second set of crowns of each of the inflow stent and each body stent of the plurality of body stents is attached to the first set of crowns of an adjacent stent via stitching.

11. A method of implanting a prosthesis within a vasculature, the method comprising:

introducing a delivery system into the vasculature of a patient, the delivery system including the prosthesis in a radially compressed configuration which is disposed within a distal portion of the delivery system, wherein the prosthesis includes a tubular graft defining a lumen that extends from an inflow end to an outflow end thereof, a prosthetic valve component disposed within the lumen of the tubular graft, an inflow stent attached to the inflow end of the tubular graft, an outflow stent attached to the outflow end of the tubular graft, and a plurality of body stents attached to the tubular graft and disposed between the inflow stent and the outflow stent, a first body stent of the plurality of body stents being disposed directly adjacent to the inflow stent and a second body stent of the plurality of body stents being disposed directly adjacent to the outflow stent, wherein a longitudinal axis of the prosthesis is defined by the lumen of the tubular graft, and wherein each of the inflow stent, the outflow stent, and each stent of the plurality of body stents is a sinusoidal patterned radially-expandable ring having a first set of crowns and a second set of crowns, the first set of crowns being disposed closer to the inflow end of the tubular graft than the second set of crowns, and wherein the second set of crowns of each of the inflow stent and each body stent of the plurality of body stents is disposed against and attached to the first set of crowns of an adjacent stent, and wherein the second body stent is oriented to extend radially outwards in a direction from the first set of crowns thereof to the second set of crowns thereof, the second body stent being oriented at a first acute angle relative to the longitudinal axis of the prosthesis, and wherein each of the first body stent, the second body stent, and the outflow stent is formed by a wire having a first diameter that is greater than a wire having a second diameter of the remaining body stents of the prosthesis;

tracking the delivery system through the vasculature to a treatment site, wherein the treatment site is one of an inferior vena cava (IVC) or a superior vena cava (SVC); and deploying the prosthesis to a radially expanded configuration at the treatment site.

12. The method of claim 11, wherein the treatment site is the inferior vena cava.

13. The method of claim 11, wherein the treatment site is the superior vena cava.

14. The method of claim 11, wherein the outflow stent is oriented substantially parallel relative to the longitudinal axis of the prosthesis.

15. The method of claim 11, wherein the first body stent is oriented to extend radially outwards in a direction from the second set of crowns thereof to the first set of crowns thereof and the first body stent is oriented at an angle between 120° and 140° relative to the longitudinal axis of the prosthesis.

16. The method of claim 11, wherein the plurality of body stents includes a third body stent and a fourth body stent disposed between the first and second body stents, the third and fourth body stents being oriented to extend substantially parallel to the longitudinal axis of the prosthesis.

17. The method of claim 11, wherein the first diameter is between 5% and 10% greater than the second diameter.

18. A method of implanting a prosthesis within a vasculature, the method comprising:

introducing a delivery system into the vasculature of a patient, the delivery system including the prosthesis in a radially compressed configuration which is disposed within a distal portion of the delivery system, wherein the prosthesis includes a tubular graft defining a lumen that extends from an inflow end to an outflow end thereof, a prosthetic valve component disposed within the lumen of the tubular graft, an inflow stent attached to the inflow end of the tubular graft, an outflow stent attached to the outflow end of the tubular graft, and a plurality of body stents attached to the tubular graft and disposed between the inflow stent and the outflow stent, a first body stent of the plurality of body stents being disposed directly adjacent to the inflow stent and a second body stent of the plurality of body stents being disposed directly adjacent to the outflow stent, wherein a longitudinal axis of the prosthesis is defined by the lumen of the tubular graft, and wherein each of the inflow stent, the outflow stent, and each stent of the plurality of body stents is a sinusoidal patterned radially-expandable ring having a first set of crowns and a second set of crowns, the first set of crowns being disposed closer to the inflow end of the tubular graft than the second set of crowns, and wherein the second set of crowns of each of the inflow stent and each body stent of the plurality of body stents is disposed against and attached to the first set of crowns of an adjacent stent, and wherein the second body stent is oriented to extend radially outwards in a direction from the first set of crowns thereof to the second set of crowns thereof, the second body stent being oriented at a first acute angle relative to the longitudinal axis of the prosthesis, and wherein the outflow stent is oriented to extend radially outwards in a direction from the first set of crowns thereof to the second set of crowns thereof, the outflow stent being oriented at a second acute angle relative to the longitudinal axis of the prosthesis, the second acute angle being less than the first acute angle;

tracking the delivery system through the vasculature to a treatment site, wherein the treatment site is one of an inferior vena cava (IVC) or a superior vena cava (SVC); and deploying the prosthesis to a radially expanded configuration at the treatment site.

19. The method of claim 18, wherein the outflow stent is oriented at an angle between 40° and 60° relative to the second body stent.

20. The method of claim 18, wherein the first body stent is oriented to extend radially outwards in a direction from the second set of crowns thereof to the first set of crowns thereof and the first body stent is oriented at an angle between 120° and 140° relative to the longitudinal axis of the prosthesis.

* * * * *